US008361979B2

(12) United States Patent
Aartsma-Rus et al.

(10) Patent No.: US 8,361,979 B2
(45) Date of Patent: Jan. 29, 2013

(54) MEANS AND METHOD FOR INDUCING EXON-SKIPPING

(75) Inventors: Annemieke Aartsma-Rus, Hoofddorp (NL); Judith Christina T. Van Deutekom, Dordrecht (NL); Garrit-Jan Boudewijn Van Ommen, Amsterdam (NL)

(73) Assignee: Academisch Ziekenhuis Leiden, Leiden (NL)

( * ) Notice: Subject to any disclaimer, the term of this patent is extended or adjusted under 35 U.S.C. 154(b) by 0 days.

(21) Appl. No.: 12/300,629

(22) PCT Filed: Mar. 18, 2007

(86) PCT No.: PCT/EP2007/054842
§ 371 (c)(1),
(2), (4) Date: Mar. 24, 2009

(87) PCT Pub. No.: WO2007/135105
PCT Pub. Date: Nov. 29, 2007

(65) Prior Publication Data
US 2009/0269755 A1  Oct. 29, 2009

(30) Foreign Application Priority Data

May 19, 2006  (EP) .................................. 06076078

(51) Int. Cl.
*C12N 15/11* (2006.01)
*C07H 21/02* (2006.01)
(52) U.S. Cl. ..................................... 514/44 A; 536/24.5
(58) Field of Classification Search ........................ None
See application file for complete search history.

(56) References Cited

U.S. PATENT DOCUMENTS

| 5,034,506 | A | | 7/1991 | Summerton et al. |
| 5,418,139 | A | | 5/1995 | Campbell |
| 5,541,308 | A | * | 7/1996 | Hogan et al. .................. 536/23.1 |
| 5,593,974 | A | | 1/1997 | Rosenberg et al. |
| 5,608,046 | A | | 3/1997 | Cook et al. |
| 5,627,263 | A | | 5/1997 | Ruoslahti et al. |
| 5,658,764 | A | | 8/1997 | Pergolizzi et al. |
| 5,741,645 | A | | 4/1998 | Orr et al. |
| 5,766,847 | A | | 6/1998 | Jackle et al. |
| 5,853,995 | A | | 12/1998 | Lee |
| 5,869,252 | A | | 2/1999 | Bouma et al. |
| 5,962,332 | A | | 10/1999 | Singer et al. |
| 5,968,909 | A | | 10/1999 | Agrawal et al. |
| 6,124,100 | A | | 9/2000 | Jin |
| 6,130,207 | A | | 10/2000 | Dean et al. |
| 6,133,031 | A | | 10/2000 | Monia et al. |
| 6,172,216 | B1 | | 1/2001 | Bennett et al. |
| 6,251,589 | B1 | | 6/2001 | Tsuji et al. |
| 6,280,938 | B1 | | 8/2001 | Ranum et al. |
| 6,300,060 | B1 | | 10/2001 | Kantoff et al. |
| 6,322,978 | B1 | | 11/2001 | Kahn et al. |
| 6,329,501 | B1 | | 12/2001 | Smith et al. |
| 6,355,481 | B1 | | 3/2002 | Li et al. |
| 6,355,690 | B1 | | 3/2002 | Tsuji |
| 6,369,038 | B1 | | 4/2002 | Blumenfeld et al. |
| 6,379,698 | B1 | | 4/2002 | Leamon |
| 6,399,575 | B1 | | 6/2002 | Smith et al. |
| 6,514,755 | B1 | | 2/2003 | Ranum et al. |
| 6,623,927 | B1 | | 9/2003 | Brahmachari et al. |
| 6,653,466 | B2 | | 11/2003 | Matsuo |
| 6,653,467 | B1 | | 11/2003 | Matsuo et al. |
| 6,670,461 | B1 | * | 12/2003 | Wengel et al. ............... 536/23.1 |
| 6,794,192 | B2 | | 9/2004 | Parums et al. |
| 6,902,896 | B2 | | 6/2005 | Ranum et al. |
| 6,982,150 | B2 | | 1/2006 | Sheetz et al. |
| 2001/0056077 | A1 | | 12/2001 | Matsuo |
| 2002/0049173 | A1 | | 4/2002 | Bennett et al. |
| 2002/0055481 | A1 | | 5/2002 | Matsuo et al. |
| 2002/0115824 | A1 | | 8/2002 | Engler et al. |
| 2002/0165150 | A1 | | 11/2002 | Ben-Sasson |
| 2003/0073215 | A1 | | 4/2003 | Baker et al. |
| 2003/0082763 | A1 | | 5/2003 | Baker et al. |
| 2003/0082766 | A1 | | 5/2003 | Baker et al. |
| 2003/0109476 | A1 | | 6/2003 | Kmiec et al. |
| 2003/0124523 | A1 | | 7/2003 | Asselbergs et al. |
| 2003/0134790 | A1 | | 7/2003 | Langenfeld |
| 2003/0235845 | A1 | | 12/2003 | van Ommen et al. |
| 2003/0236214 | A1 | | 12/2003 | Wolff et al. |
| 2004/0101852 | A1 | | 5/2004 | Bennett et al. |
| 2004/0132684 | A1 | | 7/2004 | Sampath et al. |
| 2004/0226056 | A1 | | 11/2004 | Roch et al. |
| 2005/0096284 | A1 | | 5/2005 | McSwiggen |

(Continued)

FOREIGN PATENT DOCUMENTS

| CA | 2319149 | 10/2001 |
| CA | 2526893 | 11/2004 |

(Continued)

OTHER PUBLICATIONS

Translation of WO 2005/116204.*
Partial WO2005116204, pp. 1-99, Naito et al, 2005.*
Ikezawa et al (Brain & Dev. 20: 165-168, 1998).*
Buck et al. (Biotechniques, 1999, 27:528-536).*
Aartsma-Rus et al., Molecular Therapy (2006) 14(3):401-407.
Aartsma-Rus et al., Neuromuscular Disorders (2002) 12(Suppl. 1):S71-S77.
Aartsma-Rus et al., Oligonucleotides (2005) 15(4):284-297.
International Search Report for PCT/EP2007/054842, mailed on Aug. 21, 2007, 3 pages.
International Preliminary Report on Patentability and Written Opinion for PCT/EP2007/054842, issued on Nov. 21, 2008, 8 pages.

(Continued)

*Primary Examiner* — Richard Schnizer
(74) *Attorney, Agent, or Firm* — Elizabeth Spar; Kathleen Williams; Edwards Wildman Palmer LLP

(57) ABSTRACT

In the present invention means and method are provided for optimising exon-skipping using exon-internal AON. We show that skipping efficiencies are improved by targeting putative splicing regulatory sequences (ESEs) within an exon. Such double targeting may be particularly useful for exons with which efficient skipping was difficult to obtain prior to the invention.

7 Claims, 3 Drawing Sheets

U.S. PATENT DOCUMENTS

| | | | |
|---|---|---|---|
| 2005/0222009 A1 | 10/2005 | Lamensdorf et al. | |
| 2005/0246794 A1 | 11/2005 | Khvorova et al. | |
| 2005/0277133 A1 | 12/2005 | McSwiggen | |
| 2006/0074034 A1 | 4/2006 | Collins et al. | |
| 2007/0082861 A1 | 4/2007 | Matsuo et al. | |
| 2008/0113351 A1* | 5/2008 | Naito et al. | 435/6 |

FOREIGN PATENT DOCUMENTS

| | | | |
|---|---|---|---|
| CA | 2526893 A1 | 11/2004 | |
| EP | 438512 A1 | 7/1991 | |
| EP | 558697 | 9/1993 | |
| EP | 614977 A2 | 9/1994 | |
| EP | 850300 | 7/1998 | |
| EP | 1054058 | 5/2000 | |
| EP | 1015628 A1 | 7/2000 | |
| EP | 1133993 | 9/2001 | |
| EP | 1160318 | 12/2001 | |
| EP | 1191097 | 3/2002 | |
| EP | 1191098 | 3/2002 | |
| EP | 1380644 | 1/2004 | |
| EP | 1 487 493 A2 | 12/2004 | |
| EP | 1495769 | 1/2005 | |
| EP | 1501931 | 2/2005 | |
| EP | 1544297 | 6/2005 | |
| EP | 1567667 A1 | 8/2005 | |
| EP | 1568769 | 8/2005 | |
| EP | 1619249 | 1/2006 | |
| KR | 20030035047 | 5/2003 | |
| WO | WO-9301286 | 1/1993 | |
| WO | WO-9516718 A1 | 6/1995 | |
| WO | WO-9530774 | 11/1995 | |
| WO | WO-9712899 | 4/1997 | |
| WO | WO-9730067 | 8/1997 | |
| WO | WO-9818920 A1 | 5/1998 | |
| WO | WO-9849345 A1 | 11/1998 | |
| WO | WO-0179283 A1 | 10/2001 | |
| WO | WO-0183695 | 11/2001 | |
| WO | WO-0202406 | 1/2002 | |
| WO | WO-02/24906 A1 | 3/2002 | |
| WO | WO-0224906 | 3/2002 | |
| WO | WO-0226812 A1 | 4/2002 | |
| WO | WO-0229056 | 4/2002 | |
| WO | WO-03002739 | 1/2003 | |
| WO | WO-03/014145 A2 | 2/2003 | |
| WO | WO-03013437 | 2/2003 | |
| WO | WO-03037172 | 5/2003 | |
| WO | WO-03095647 | 11/2003 | |
| WO | WO-2004/011060 A2 | 2/2004 | |
| WO | WO-2004015106 | 2/2004 | |
| WO | WO-2004016787 | 2/2004 | |
| WO | WO-2004048570 | 6/2004 | |
| WO | WO 2004/083432 * | 9/2004 | |
| WO | WO-2004083432 | 9/2004 | |
| WO | WO-2004083446 | 9/2004 | |
| WO | WO-2004101787 | 11/2004 | |
| WO | WO-2004108157 | 12/2004 | |
| WO | WO-2004108157 A2 | 12/2004 | |
| WO | WO-2005019453 A2 | 3/2005 | |
| WO | WO-2005035550 | 4/2005 | |
| WO | WO-2005085476 A1 | 9/2005 | |
| WO | WO-2005086768 | 9/2005 | |
| WO | WO-2005105995 A2 | 11/2005 | |
| WO | WO-2005115439 | 12/2005 | |
| WO | WO-2005116204 A1 | 12/2005 | |
| WO | WO-2006/000057 | 1/2006 | |
| WO | WO-2006007910 | 1/2006 | |
| WO | WO-2006017522 | 2/2006 | |
| WO | WO-2006031267 A2 | 3/2006 | |

OTHER PUBLICATIONS

Aartsma-Rus et al. Therapeutic Modulation of DMD splicing by Blocking Exonic Splicing Enhancer Sites with Antisense Oligonucleotides Ann NY Acad Sci 2006 pp. 74-76 vol. 1082.

Aartsma-Rus, et al., Antisense-Induced Multiexon Skipping for Duchenne Muscular Dystrophy Makes More Sense, Am. J. Hum. Genet, 2004 pp. 83-92, vol. 74.

Aartsma-Rus, et al., Exploring the Frontiers of Therapeutic Exon Skipping for Duchenne Muscular Dystrophy by Double Targeting within One or Multiple Exons, Molecular Therapy, 2006, pp. 1-7.

Aartsma-Rus, et al., Targeted exon skipping as a potential gene correction therapy for Duchenne muscular dystrophy, Neuromuscular Disorders, 2002, S71-S77, vol. 12.

Aartsma-Rus, et al., Therapeutic antisense-induced exon skipping in cultured muscle cells from six different patients, Human Molecular Genetics, 2003, pp. 907-914, vol. 12, No. 8.

Abbs et al., A convenient multiplex PCR system for the detection of dystrophin gene deletions: a comparative analysis with cDNA hybridisation shows mistypings by both methods, J. Med. Genet, 1991, pp. 304-311, vol. 28.

Agrawal and Kandimalla, et al., "Antisense therapeutics: is it as simple as complementary base recognition?" Mol. Med. Today, Feb. 2000, vol. 6., pp. 72-81.

Anderson et al., Correlated NOS-I[mu] and myf5 expression by satellite cells in mdx mouse muscle regeneration during NOS manipulation and deflazacort treatment. Neuromuscular Disorders, Jun. 2003, vol. 13(5): 388-396.

Arzumanov, et al. Inhibition of HIV-1 Tat-dependent trans activation by steric block chimeric 2'-O-methyl/LNA oligoribonucleotides. Biochemistry, 2001, vol. 40, pp. 14645-14654.

Austin et al. "Cloning and characterization of alternatively spliced isoforms of Dp71." *Hum Mol Genetics* 1995 vol. 4 No. 9 1475-1483.

Australian Office Action for AU 2009240879, dated Jun. 22, 2011.

Barabino et al. (1992) "Antisense probes targeted to an internal domain in US snRNP specifically inhibit the second step of pre-mRNA splicing" Nucleic Acids Res. 20(17):4457-4464.

Bionity.Com News-Center, Leiden University Medical Center and Prosensa B.V. Announce First Successful Clinical Study with RNA-based Therapeutic PRO051, dated Jan. 3, 2008, <http://www.bionity.com/news/e/76185>.

Biopharmaceutiques, Merging Pharma & Biotech, Edition 48, Jan. 10, 2008. <http://www.biopharmaceutiques.com/en/num>, visited Jan. 11, 2008.

Bremmer-Bout, et al., Targeted exon skipping in transgenic hDMD mice: A model for direct preclinical screening of human-specific antisense oligonucleotides. Mol Ther. Aug. 2004; 10(2):232-40.

Brett et al., EST comparison indicates 38% of human m RNAs contain possible alternative splice forms. FEBS Lett 474(1): 83-86. (2000).

Brown, et al., "Structure and mutation of the dystrophin gene" in Dystrophin: Gene, protein and cell biology, (Brown and Lucy, eds). Cambridge University Press, Cambridge, 1997, pp. 1-16.

Canadian Office Action for CA 2,524,255, dated Jul. 6, 2011.

Cartegni, et al., Abstract, Listening to silence and understanding nonsense: exonic mutations that affect splicing, Nature Reviews Genetics, Apr. 2002, pp. 285-298, vol. 3.

Chaubourt et al., Muscular nitric oxide synthase ([mu]NOS) and utrophin. J. of Physiology Paris, Jan.-Mar. 2002; vol. 96(1-2): 43-52.

Coulter et al. Identification of a new class of exonic splicing enhancers by in vivo selection. Mol. Cell. Biol. 17(4) 2143-50 (1997).

Crooke. In Basic Principles of Antisense Therapeutics, Springer-Verlag, Eds, New York, 1998, pp. 1-50.

Dahlqvist, et al., "Functional notch signaling is required for BMP4-induced inhibition of myogenic differentiation," Development 130:6089-6099 (2003).

De Angelis, et al., Chimeric snRNA molecules carrying antisense sequences against the splice junctions of exon 51 of the dystrophin pre-mRNA exon skipping and restoration of a dystrophin synthesis in delta 48-50 DMD cells, PNAS, Jul. 9, 2002, pp. 9456-9461, vol. 99, No. 14.

Declaration of Dr. Adrian Krainer (submitted in Third Party's Stmt for JP Appl. No. 2002-529499, dated Oct. 29, 2010).

Dickson, et al., Screening for antisense modulation of dystrophin pre-mRNA splicing, Neuromuscul. Disord., 2002, S67-70, Suppl. 1.

Dirkson, et al., Mapping the SF2/ASF Binding Sites in the Bovine Growth Hormone Exonic Splicing Enhancer, The Journal of Biological Chemistry, Sep. 15, 2000, pp. 29170-29177, vol. 275, No. 37.

Dunckley, et al., Modification of splicing in the Dsytrophin gene in cultured Mdx muscle cells by antisense oligoribonucleotides. Hum Mol Genet. 1995 7(7):1083-90.

Dunckley, et al., Modulation of Splicing in the DMD Gene by Antisense Oligoribonucleotides, Nucleosides & Nucleotides, 1997, pp. 1665-1668, vol. 16, No. 7-9.

EP Office Action dated Jan. 29, 2007.

Erba et al., Structure, chromosome location, and expression of the human gamma-actin gene: differential evolution, location, and expression of the cytoskeletal beta- and gamma-actin genes. Mol. Cell. Biology, 1988, 8(4):1775-89.

Errington, et al., Target selection for antisense oligonucleotide induced exon skipping in the dystrophin gene. J Gene Med. Jun. 2003; 5(6):518-27.

Feener et al., Alternative splicing of human dystrophin mRNA generates isoforms at the carboxy terminus. Nature, 338 (6215): 509-511 (1989).

Fluiter, K., "In Vivo tumor growth inhibition and biodistribution studies of locked nucleic acid (LNA) antisense oligonucleotides," Nucl. Acids Research 2003, vol. 31., No. 3., pp. 953-962.

Genes VII, Jan. 2000, Benjamin Lewin, Chapter 22, Nuclear Splicing, pp. 704-705.

Ginjaar, et al., Dystrophin nonsense mutation induces different levels of exon 29 skipping and leads to variable phenotypes within one BMD family, European Journal of Human Genetics (2000) 8, 793-796.

Granchelli et al., Pre-clinical screening of drugs using the mdx mouse. Neuromuscular Disorders, Pergamon Pres. vol. 10(4-5): 235-239, Jun. 2000.

Gryaznov, "Oligonucleotide N3'→ P5' phosphoramidates as potential therapeutic agents." Biochemistry et Biophys. Acta, 1999, vol. 1489, pp. 131-140/.

Hagiwara, et al. "A novel point mutation (G-1 to T) in a 5' splice donor site of intron 13 of the dystrophin gene results in exon skipping and is responsible for Becker muscular dystrophy." Am J. Hum Genet. Jan. 1994;54(1):53-61.

Hussey, et al., Analysis of five Duchenne muscular dystrophy exons and gender determination using conventional duplex polymerase chain reaction on single cells, Molecular Human Reproduction, 1999, pp. 1089-1094, vol. 5, No. 11.

Iezzi, et al. "Deacetylase inhibitors increase muscle cell size by promoting myoblast recruitment and fusion through induction of follistation," Development Cell 6:673-684 (2004).

International Preliminary Examination Report, International Application No. PCT/NL01/00697, dated Aug. 1, 2002.

International Search Report, International Application No. PCT/NL 2008/050470, dated Jul. 2, 2009.

International Search Report, International Application No. PCT/NL 2008/050475, dated Jun. 25, 2009.

International Search Report, International Application No. PCT/NL 2008/050673, dated Feb. 9, 2009.

International Search Report, International Application No. PCT/NL01/00697, dated Dec. 21, 2002.

International Search Report, International Application No. PCT/NL2004/000196, dated Oct. 28, 2004.

International Search Report, International Application No. PCT/NL2006/000209, dated Oct. 5, 2006.

Karras, et al., Deletion of Individual Exons and Induction of Soluble Murine Interleukin-5 Receptor-alpha Chain Expression through Antisense Oligonucleotide-Mediated Redirection of Pre-mRNA Splicing, Molecular Pharmacology, 2000, pp. 380-387, vol. 58.

Kerr, et al., "Bmp Regulates Skeletal Myogenesis at Two Steps," Molecular Cellular Proteomics 2.9:976. 123.8 (2003) (Abstract Only).

Kurrek, et al., "Design of antisense oligonucleotides stabilized by locked nucleic acids." Nucleic Acids Research, 2002, vol. 30, No. 9, pp. 1911-1918.

Laptev et al., (1994) "Specific inhibition of expression of a human collagen gene (COL1A1) with modified antisense oligonucleotides. The most effective target sites are clustered in double-stranded regions of the predicted secondary structure for the mRNA" Biochemistry 33(36):11033-11039.

Lee et al., Receptor mediated uptake of peptides that bind the human transferin receptor. Eur. J. Biochem. 268, 2004-2012 (2001).

Leiden University Medical Center and Prosensa B.V. Announce New England Journal of Medicine Publication of First Successful Clinical Study with RNA-based Therapeutic PRO051 in Duchenne Muscular Dystrophy, Dec. 27, 2007.

Letter from Katholieke Universiteit Leuven to Dr. N. Goemans, Child Neurology, UZ dated Jan. 22, 2008, regarding a Phase I/II, open label, escalating dose, pilot study to assess the effect, safety, tolerability and pharmacokinetics of multiple subcutaneous doses of PRO051 in patients with Duchenne muscular dystrophy. PRO051-02 (translation provided).

Letter from Prosensa Therapeutics B.V. to Federal Agency for Medicines and Health Products dated Jan. 9, 2008, regarding a Phase I/II, open label, escalating dose, pilot study to assess the effect, safety, tolerability and pharmacokinetics of multiple subcutaneous doses of PRO051 in patients with Duchenne muscular dystrophy.

Liu et al., "A mechanism for exon skipping caused by nonsense or missense mutations in BRCA1 and other genes." Nat Genet. Jan. 2001;27(1):55-8.

Liu, et al., Identification of functional exonic splicing enhancer motifs recognized by individual SR proteins, Genes & Development, 1998, pp. 1998-2012, vol. 12.

Lu et al. Functional Amounts of Dystrophin Produced by Skipping the Mutated Exon in the MDX Dystrophic Mouse 2003 Nat Med 8: 1009-1014.

Lu, et al., Massive Idiosyncratic Exon Skipping Corrects the Nonsense Mutation in Dystrophic Mouse Muscle and Produces Functional Revertant Fibers by Clonal Expansion, The Journal Cell Biology, Mar. 6, 2000, pp. 985-995, vol. 148, No. 5.

LUMC and Prosensa report positive results of DMD study, Pharmaceutical Business Review Onlin, dated Dec. 28, 2007, <http://www.pharmaceutical-business-review.com/article_news_print.asp?guid=8462FD44-F35D-4EOB-BC>.

Mann, et al., Antisense-induced exon skipping and synthesis of dystrophin in the mdx mouse. Proc Natl Acad Sci USA Jan. 2, 2001: 98(1):42-7.

Mann, et al., Improved antisense oligonucleotide induced exon skipping in the mdx mouse model of muscular dystrophy. J Gene Med. Nov.-Dec. 2002:4(6):644-54.

Matsuo et al. (1992) "Partial deletion of a dystrophin gene leads to exon skipping and to loss of an intra-exon hairpin structure from the predicted mRNA precursor" Biochem. Biophys. Res. Commun. 182(2):495-500.

Matsuo, et al., "Duchenne/Becker muscular dystrophy: from molecular diagnosis to gene therapy." Brain Dev. (1996) 18(3):167-172.

Monaco, et al., An Explanation for the Phenotypic Differences between Patients Bearing Partial Deletions of the DMD Locus, Genomics, 1988, pp. 90-95, vol. 2.

Moon, et. al., "Target site Search and effective inhibition of leukaemic cell growth by a covalently closed multiple anti-sense oligonucleotide to c-myb" The Biochemical Journal, Mar. 1, 2000, vol. 346 Pt 2, pp. 295-303.

Munroe (1988) "Antisense RNA inhibits splicing of pre-mRNA in vitro" EMBO J. 7(8):2523-2532.

Muntoni et al. "A Mutation in the Dystrophin Gene Selectively Affecting Dystrophin Expression in the Heart." J. Clin Invest. vol. 96 Aug. 1995. 693-699.

New Clinical Trial Results Show How Personalized Medicine Will Alter Treatment of Genetic Disorders, Medical News Today, Dec. 29, 2007 <http://www.medicalnewstoday.com/article/92777.php>.

Nishio, et al., Identification of a novel first exon in the human dystrophin gene and of a new promoter located more than 500 kb upstream of the nearest known promoter. (1994) J. Clin. Invest. 94:1037-1042.

Notice of Opposition filed against EP 1 619 249 B, dated Jun. 23, 2009.

Office Action for U.S. Appl. No. 10/395,031, dated Apr. 2, 2009.
Office Action for U.S. Appl. No. 10/395,031, dated Aug. 23, 2007.
Office Action for U.S. Appl. No. 10/395,031, dated Feb. 6, 2006.
Office Action for U.S. Appl. No. 10/395,031, dated Jul. 8, 2005.
Office Action for U.S. Appl. No. 10/395,031, dated May 30, 2008.
Office Action for U.S. Appl. No. 10/395,031, dated Nov. 30, 2006.
Office Action for U.S. Appl. No. 10/395,031, dated Oct. 16, 2009.
Office Action for U.S. Appl. No. 11/233,495, dated Dec. 1, 2008.

Office Action for U.S. Appl. No. 11/233,495, dated Jun. 25, 2009.
Office Action for U.S. Appl. No. 11/233,507, dated Jun. 15, 2007.
Office Action for U.S. Appl. No. 11/233,507, dated Mar. 19, 2008.
Office Action for U.S. Appl. No. 11/233,507, dated Nov. 12, 2008.
Office Action for U.S. Appl. No. 11/982,285, dated May 4, 2009.
Office Action for U.S. Appl. No. 11/982,285, dated Sep. 18, 2009.
Opalinska and Gewirtz. "Nucleic-acid therapeutics: basic principles and recent applications." Nature Reviews Drug Discovery, 2002, vol. 1, pp. 503-514.
Oxford Dictionary of English, 2nd Edition, Revised, Oxford University Press, p. 158, 2005.
Patel, et al., "The Function of Myostatin and strategies of Myostatin blockade-new hope for therapies aimed at promoting growth of skeletal muscle," Neuromuscular Disorders 15(2):117-126 (2005).
Patentee's response during prosecution of opposed patent, dated Jan. 27, 2010.
Pramono, et al., Abstract, Induction of Exon Skipping of the Dystrophin Transcript in Lymphoblastoid Cells by Transfecting an Antisense Oligodeoxynucleotide Complementary to an Exon Recognition Sequence, Biochemical and Biophysical Research Communications, Sep. 13, 1996, pp. 445-449, vol. 226, No. 2.
Rando, Thomas A., "Oligonucleotide-mediated gene therapy for muscular dystrophies." Neuromuscular Disorders, 2002, vol. 12, pp. S55-S60.
Request for an Opinion under Section 74(A) in relation to Patent No. EP (UK) 1 619 249B in the name of Academisch Ziekenhuis Leiden, opinion issued on Jun. 4, 2009.
Request for UK IPO Opinion (Section 74A & Rule 93)—EP(UK) 1619249 dated Mar. 9, 2009.
Roberts et al., Direct detection of dystrophin gene rearrangements by analysis of dystrophin mRNA in peripheral blood lymphocytes. Am. J. Hum. Genet. 49(2): 298-310 (1991).
Roberts, et al., "Exon structure of the human dystrophin gene." Genomics, 1993, vol. 16, No. 2, pp. 536-538. (1993).
Roberts, et al., Direct diagnosis of carriers of Duchenne and Becker muscular dystrophy by amplification of lymphocyte RNA. Lancet, 336 (8730-8731): 1523-6 (1990).
Roberts, et al., Searching for the 1 in 2,400,000: a review of dystrophin gene point mutations. Hum. Mut. 4:1-11 (1994).
Scanlon, "Anti-genes: siRNA, ribozymes, and antisense." Curr. Pharmaceutical Biotechnology, 2004, vol. 5, pp. 415-420.
Segalat et al., Capon expression in skeletal muscle is regulated by position, repair, NOS activity, and dystrophy. Experimental Cell Research, Jan. 2005, vol. 302(2): 170-179.
Sertic, et al., "Deletion screening of the Duchenne/Becker muscular dystrophy gene in Croatian population" Coll. Antropol. 1997, 1:151-156.
Shapiro and Senapathy, "RNA splice junctions of different classes of eukaryotes: sequence statistics and functional implications in gene expression." Nucleic Acids Research, 1987, vol. 15. No. 17, pp. 7155-7174.
Sherratt, et al., Exon Skipping and Translation in Patients with Frameshift Deletions in the Dystrophin Gene, Am. J. Hum. Genet, 1993, pp. 1007-1015, vol. 53.
Shiga, et al., Disruption of the Splicing Enhancer Sequence within Exon 27 of the Dystrophin Gene by a Nonsense Mutation Induces Partial Skipping of the Exon and Is Responsible for Becker Muscular Dystrophy, J. Clin. Invest., Nov. 1997, pp. 2204-2210, vol. 100, No. 9.
Simoes-Wust, et al., bcl-xL Antisense Treatment Induces Apoptosis in Breast Carcinoma Cells, Int. J. Cancer, 2000, pp. 582-590, vol. 87.
Sterrenburg, et al., "Gene expression of profiling highlights defective myogenesis in DMD patients and a possible role for bone morphogenetic protein 4," Neurobiology of Disease 23(1):228-236 (2006).
Surono et al. Chimeric RNA/ethylene-Bridged Nucleic Acids Promote Dystrophin Expression in Myocytes of Duchenne Muscular Dystrophy by Inducing Skipping of the Nonsense Mutation-Encoding Exon Hum Gene Ther. vol. 15(8) pp. 749-757 (2004).
Surono et al. "Six Novel Transcripts that Remove a Huge Intron Ranging from 250 to 800 kb Are Produced by Alternative Splicing of the 5' Region of the Dystrophin Gene in Human Skeletal Muscle." BBRC 239 895-899 (1997).

Suter, et al., Double-target antisense U7 snRNAs promote efficient skipping of an aberrant exon in three human B-thalassemic mutations, Human Molecular Genetics, 1999, pp. 2415-2423, vol. 8, No. 13.
Suwanmanee et al. (2002) "Restoration of Human b-globin Gene Expression in Murine and Human IVS2-654 Thalassemic Erythroid Cells by Free Uptake of Antisense Oligonucleotides" Mol. Pharmacology 62(3):545-553.
Takashima et al. Oligonucleotides Against a Splicing Enhancer Sequence Led to Dystrophin Production in Muscle Cells From a Duchenne Muscular Dystrophy Patient Brain Dev 2001 (December); 23:788-90.
Takeshima, et al., Modulation of In Vitro Splicing of the Upstream Intron by Modifying an Intra-Exon Sequence Which is Deleted from the Dystrophin Gene in Dystrophin Kobe, J. Clin. Invest., Feb. 1995, pp. 515-520, vol. 95.
Tanaka, et al., Polypurine Sequences within a Downstream Exon Function as a Splicing Enhanced, Molecular and Cellular Biology, Feb. 1994, pp. 1347-1354, vol. 14, No. 2.
Thanh, et al., "Characterization of revertant muscle fibers in Duchenne muscular dystrophy, using exon-specific monoclonal antibodies against dystrophin." Am. J. Hum. Genet. 1995, vol. 56, pp. 725-731.
Third Party's Statement for Japan Appl. No. 2002-529499, dated Oct 29, 2010.
Tian H, Kole R, "Selection of novel exon recognition elements from a pool of random sequences." Mol Cell Biol 15(11):6291-8. (1995).
Tsuchida "Peptides, Proteins & Antisense: the role of myostatin and bone morphogenetic proteins in muscular disorders," Expert Opinion of Biologica Therapy 6(2):147-153 (2006).
Van Deutekom et al. Advances in Duchenne Muscular Dystrophy Gene Therapy 2003 Nat Rev Genet 4(10): 774-83.
Van Deutekom, et al., Antisense-induced exon skipping restores dystrophin expression in DMD patient derived muscle cells. Hum Mol Genet. 2001 Jul. 15, 2001:10(15:1547-54).
Watakabe, et al., The role of exon sequences in splice site selection, Genes & Development, 1993, pp. 407-418, vol. 7.
Wells et al. Enhanced in Vivo Delivery of Antisense Oligonucleotide to Restore Dystrophin Expression in Adult MDX Mouse Muscle FEBS Letters 2003 552: 145-149.
Wheway and Roberts. "The Dystrophin Lymphocyte promoter revisited: 4.5-megabase intron, or artefact?" *Neuromuscular Disorders* 13(2003) 17-20.
Wilton, et al., "Specific removal of the nonsense mutation from the mdx dystrophin protein mRNA using antisense oligonucleotides." Neuromuscular Disorders, 1999, vol. 9, pp. 330-338.
Wilton, et al., "Antisense oligonucleotides, exon skipping and the dystrophin gene transcript," Acta Myologica XXIV:222-229 (2005).
Alter et al., "Systemic delivery of morpholino oligonucleotide restores dystrophin expression bodywide and improves dystrophic pathology." *Nature Medicine.* Feb. 2006;12(2):175-7. Epub Jan. 29, 2006.
Austin, et al., "Expression and synthesis of alternatively spliced variants of Dp71 in adult human brain." *Neuromuscular Disorders*, 10(2000) 187-193.
Barany "The ligase chain reaction in a PCR world." *PCR Methods Appl.* Aug. 1991;1(1):5-16.
Caplen, et al., "Rescue of polyglutamine-mediated cytotoxicity by double-stranded RNA-mediated RNA interference," *Human molecular genetics*, 2002, pp. 175-184, vol. 11, No. 2.
Denny et al., "Oligo-riboprobes. Tools for in situ hybridisation". *Histochemistry* (1988) 89:481-493.
Fu, et al., "An Unstable Triplet Repeat in a Gene Related to Myotonic Muscular Dystrophy", *Science*, vol. 255, 1256-1258. 1992.
Furling. et al., "Viral vector producing antisense RNA restores myotonic dystrophy myoblast functions", *Gene Therapy* (2003) 10, 795-802.
Galderisi, et al., "Myotonic dystrophy: antisense oligonucleotide inhibition of DMPK gene expression in vitro." *Biochem Biophys Res Commun* 221 :750-754 (1996).
Handa, et al., "The AUUCU repeats responsible for spinocerebellar ataxia type 10 form unusual RNA hairpins." *Journal of Biological Chemistry* 280(32):29340-29345 (2005).

Hasholt, et al., "Antisense downregulation of mutant huntingtin in a cell model," *Journal of Gene Medicine*, 2003, pp. 528-538, vol. 5, No. 6.
Highfield "Science: Boffin log", The Daily Telegraph, http://www.telegraph.co.uk/science/science-news/3320286/Science-Boffin-log.html, (Hope for Muscular Dystrophy Drug) Jan. 1, 2008.
Hoffman, et al. ,"Somatic reversion/suppression of the mouse *mdx* phenotype in vivo." *J. of the Neurological Sciences*, 1990, 99: 9-25.
International Search Report for PCT/NL2009/050006 dated Jul. 31, 2009.
Ito, et al., "Purine-Rich Exon Sequences Are Not Necessarily Splicing Enhancer Sequence in the Dystrophin Gene." *Kobe J. Med. Sci.* 47, 193/202, Oct. 2001.
Langlois, et al., "Hammerhead ribozyme-mediated destruction of nuclear foci in myotonic dystrophy myoblasts," *Molecular therapy*, 2003, pp. 670-680, vol. 7, No. 5.
Liu, et al., "Specific inhibition of Huntington's disease gene expression by siRNAs in cultured cells", *Proc. Japan Acad.* 79, Ser. B (2003), 293-298.
Matsuo, et al., Exon Skipping during Splicing of Dystrophin mRNA Precursor due to an Intraexon Deletion in the Dystrophin Gene of Duchenne Muscular Dystrophe Kobe. *J. Clin. Invest.* 87, 2127-2131. 1991.
Office Action for U.S. Appl. No. 11/233,507, dated May 29, 2009.
Politano et al., "Gentamicin administration in Duchenne patients with Premature stop codon. Preliminary results." *Acta Myologica* 22:15-21, 2003.
Reitter B. "Deflazacort vs. prednisone in Duchenne muscular dystrophy: trends of an ongoing study." *Brain Dev.* 1995;17 Suppl:39-43.
Smith et al., "Muscle-specific peptide #5", Mar. 23, 1999. From http://www.ebi.ac.uk/cgi-bin/epo/epofetch?AAW89659, downloaded Jul. 16, 2007. XP 002442550.
Takeshima et al "Intravenous Infusion of an Antisense Oligonucleotide Results in Exon Skipping in Muscle Dystrophin mRNA of Duchenne Muscular Dystrophy." *Pediatric Research*. May 2006, 59, 5, p. 690-694.
Treat-NMD Neuromuscular Network, Jan. 11, 2008.
Vickers, et al., "Efficient reduction of target RNAs by small interfering RNA and RNase H-dependent antisense agents. A comparative analysis." *J. Biol. Chem.* 278(9):7108-7118 (2003).
Wang et al. "Adeno-associated virus vector carrying human minidystrophin genes effectively ameliorates muscular dystrophy in mdx mouse model", Dec. 5, 2000, *P.N.A.S.* 97(25):13714-13719.
Yen, et al., "Sequence-specific cleavage of Huntingtin MRNA by catalytic DNA," *Animals of Neurology*, 1999, pp. 366-373, vol. 46, No. 3.
Aartsma-Rus et al. "Guidelines for Antisense Oligonucleotide Design and Insight into Splice-modulation Mechanisms." *Molecular Therapy 2009* pp. 548-553 (Published Online Sep. 23, 2008).
Duboc et al., "Effect of Perindopril on the Onset and Progression of Left Ventricular Dysfunction in Duchenne Muscular Dystrophy." *Journal of Amer. Coll. Cardiology*, 45(6):855-7, Mar. 15, 2005.
GenBank accession No. AZ993191.1, 2MO278E12F mouse 10kb plasmid UUGC2M library Mus muscu genomic clone UUGC2MO278E12F, genomic survey sequence, entry created and last updated on Apr. 27, 2001.
GenBank accession No. EW162121.1, rfat0126_k17.y1 fat Sus scrofa cDNA5-, mRNA sequence, entry created on Aug. 13, 2007, last updated on Mar. 3, 2011.
O'Shaughnessy et al., "Superior Survival With Capecitabine Plus Docetaxel Combination Therapy in Anthracycline-Pretreated Patients With Advanced Breast Cancer: Phase III Trial Results." *Journal of Clinical Oncology*, vol. 20, No. 12 Jun. 15, 2002: pp. 2812-2823.
Rosen et al., "Combination Chemotherapy and Radiation Therapy in the Treatment of Metastatic Osteogenic Sarcoma." *Cancer* 35: 622-630, 1975.
Verhaart et al., "Prednisolone treatment does not interfere with 2OmePS antisense-mediated exon skipping in DMD." Human Gene Therapy. Mar. 2012, 23(3): 262-273. doi:10.1089/hum.2011.127.

\* cited by examiner

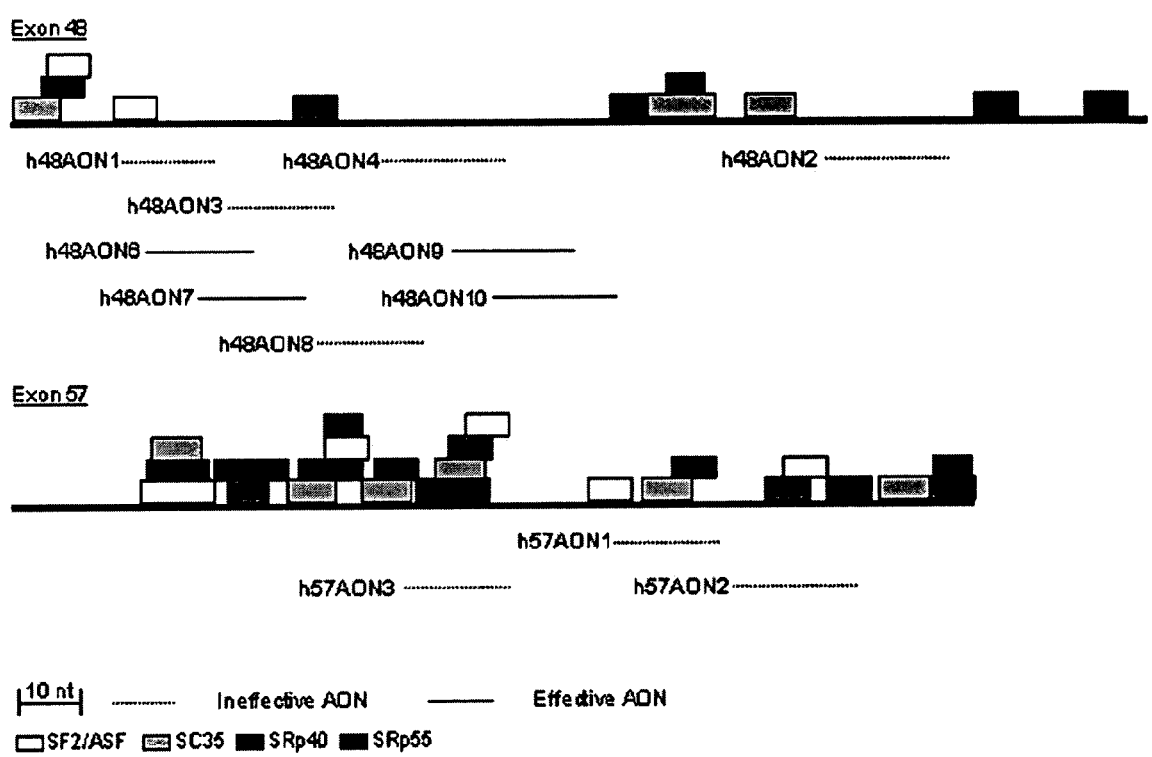
Fig. 1A, contd.

MEANS AND METHOD FOR INDUCING EXON-SKIPPING

CROSS-REFERENCE TO RELATED APPLICATIONS

This application is the national phase of PCT application PCT/EP2007/054842 having an international filing date of 18 May 2007, which claims benefit of European patent application No. 06076078.2 filed 19 May 2006. The contents of the above patent applications are incorporated by reference herein in their entirety.

REFERENCE TO SEQUENCE LISTING SUBMITTED VIA EFS-WEB

This application is being filed electronically via the USPTO EFS-WEB server, as authorized and set forth in MPEP §1730 II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows:

| File Name | Date of Creation | Size (bytes) |
| --- | --- | --- |
| 313632005300Seqlist.txt | Mar. 23, 2009 | 29,507 bytes |

The invention relates to oligonucleotides and equivalents thereof and the use thereof for inducing exclusion of exons from mRNA.

Anti-sense technology has developed considerably in recent years. The general field of anti-sense technology can be divided into several areas. One of these area's is the field of exon skipping.

In this field, small molecules are added to the cell to specifically interfere with the splicing of one messenger RNA (mRNA) and more specifically, with the incorporation of, or the rather the lack of incorporation of a specific exon in the mature mRNA.

In the field of exon skipping, two general approaches can be distinguished. One approach focuses on interfering with enzymatic process of splicing, i.e. the physical joining of exonic sequences. The other approach relies on interfering with the 'logistics' of the splicing process, i.e. the recognition of exons by the splicing machinery. Both approaches use small molecules to obtain the desired effects. The small molecules all share the characteristic of nucleic acids to be able to 'hybridise' to complementary sequences. Examples of such small molecules are, of course, RNA and DNA, and also modified RNA and DNA such as LNA and morpholinos and nucleic acid mimics such as PNA. These molecules are further referred to by the general term small molecules or the more frequently used term anti-sense oligonucleotide (AON).

The small molecules are thought to act by hybridising to specific locations on the pre-mRNA. The hybridisation is thought to interfere with either the enzymatic process of splicing or the recognition of exons.

At present, exon skipping focuses on the specific exclusion of one or more exons from the mature mRNA. However, it is also possible to redirect the splicing machinery such that other exons are included into the mRNA. This approach is, for instance, of use in genes that are subject to alternative splicing. In these situations, small molecules can be designed redirecting the splicing machinery such that a specific alternative is more efficiently made.

In the present invention it has been found that the exon-skipping process can be made more efficient. Much of the earlier work on exon skipping was done using AONs that were directed toward exon skipping in the dystrophin gene. To date we have identified a series of 114 exon-internal AONs to induce the skipping of 35 exons in cultured muscle cells (14). Our data suggest that effective exon-internal AONs are likely to act by steric hindrance of binding of a member of the serine/arginine-rich (SR) protein family to exonic splicing enhancer (ESE) sites (15). SR proteins bind to exonic sequence motives and recruit other splicing factors to mediate splicing (19). For most exons that we studied, AON-targeting of a single ESE was sufficient to induce significant levels of exon skipping (14). However, for some exons the skipping efficiencies were low to zero. In the present invention we demonstrated that skipping levels are improved by targeting an exon with two or more exon internal AON. To this end the invention provides a method for determining whether the efficiency can be increased with which an exon is excluded from a mature mRNA in a cell that produces an exon containing precursor of said mRNA
said method comprising
providing said cell with a first anti-sense oligonucleotide (AON) that can hybridise to an exon internal part of said exon, and determining whether said efficiency is increased upon providing said cell with a second AON that can hybridise to another exon internal part of said exon. The efficiency increase is preferably determined by comparing the level with the efficiency of either AON alone. The term increased efficiency as used herein refers to the situation wherein (i) the amount of mRNA from which the targeted exon is excluded is higher than with either AON alone, or wherein (ii) the time span within which exclusion of the targeted exon can be detected in said cell is increased or (iii) a combination of both. A method of the invention also provides additional robustness when compared to a method of exon skipping using a single AON. The invention therefore further provides a method for inducing exon skipping in a pre-mRNA that is produced by a cell comprising providing said cell with at least two AON that can hybridise to different exon internal parts of an exon on said pre-mRNA and culturing said cell to allow splicing of said pre-mRNA.

A sequence is usually referred to as an exon because the sequence is part of a pre-mRNA that ends up in a mature mRNA. A pre-mRNA contains at least one intron. The first exon contains the cap-site whereas the last exon typically contains the polyA signal. In the present invention exon skipping is preferentially directed to internal exons. An internal exon is any one of exons 2 to exon n−1, wherein n is the total number of exons in said pre-mRNA. When an exon is skipped it is no longer included into a mature mRNA. This feature could be viewed by some as to imply that the sequence is no longer an exon but rather a (part of) an intron. An exon is therefore defined herein as a sequence present in a pre-mRNA, that is incorporated into a mature mRNA by the splicing machinery of the cell that is expressing said pre-mRNA, when said cell is not provided with an AON that induces skipping of said exon. A method of exon skipping in the present invention is therefore also referred to as a method for changing an exonic sequence into an intronic sequence, alternatively, a method of the invention is a method for masking an exonic sequence such that, when masked, said exonic sequence is no longer recognized as an exon by the splicing machinery of a cell.

A cell can be provided with an AON in a number of different ways. In a preferred embodiment said AON is provided to said cell by incorporating said AON into a gene delivery vehicle, preferably a liposome. In another preferred embodiment said AON is provided to said cell by means of a vector that expresses said AON or a precursor thereof. In a preferred embodiment said vector comprises a viral vector, preferably an adeno-associated virus vector. Thus the invention further provides a gene delivery vehicle comprising at least two exon internal AON specific for the same exon.

Using at least two exon internal AON specific for the same exon to skip said exon makes a method of the invention more robust. Moreover, it allows efficient skipping of exons that do not skip efficiently when using only one AON. Without being bound by theory it is believed that an exon-internal AON induces skipping of an exon by hindering the binding of so-called SR (Ser-Arg) proteins that bind to exonic splice enhancer (ESE) sites. In the present invention it was found among others that exons can contain so-called independent ESE sites. This means that when the activity of one ESE site is blocked or hindered by, for instance, the presence of an AON on said exon, another independent ESE on said exon remains functional. As this ESE remains functional, the exon is still efficiently incorporated into the mRNA. This effect can be counteracted by targeting all of the independent ESE sites on said exon. In this case essentially all of the ESE sites are targeted by an AON thereby blocking or hindering binding of SR proteins to said ESE sites which subsequently leads to efficient skipping of the thus targeted exon. Blocking or hindering of an ESE site can be achieved in various ways. For instance, hybridisation of said AON can alter the secondary structure of the exon such that SR proteins can no longer bind to said ESE site. In a preferred embodiment said AON overlaps at least part of a predicted ESE site on the targeted exon. In this way binding of SR proteins to said site is sterically blocked by the hybridisation of said AON thereto. It is preferred that said AON overlaps at least one predicted ESE site. As predicted ESE sites have a tendency to cluster it is preferred that, said AON overlaps at least two and preferably at least three predicted ESE sites on said exon. Thus in a preferred embodiment a hybridisation site of said first AON on RNA of said exon overlaps at least one predicted ESE site on said exon RNA. Preferably, said a hybridisation site of said second AON on said exon RNA overlaps at least one predicted ESE site on said exon RNA.

It is not preferred to target said first and said second AON to a single predicted ESE site on said exon RNA. Although this might be the case, it is preferred that said first AON targets a different ESE than said second AON. This can be achieved in various ways. Targeting of the same ESE is preferably avoided by avoiding significant overlap in the hybridisation sites of said AON on said exon RNA. Thus preferably a hybridisation site of said first AON and a hybridisation site of said second AON exhibit less than 5 consecutive nucleotides overlap. More preferably, said sites have less than 3 and more preferably less than 1 or no overlap. Such overlap can easily be avoided by selection of the AON. As an AON of the invention preferably has a linear and continuous hybridisation site on said exon RNA, overlap is preferably avoided by avoiding significant sequence identity in the used AONs. In this respect it is preferred that said first and said second AON have less than 5 consecutive nucleotides sequence identity. Preferably said first and said second hybridisation site on said exon RNA have less than 3 consecutive nucleotides overlap, more preferably less than 2, and preferably less than 1 nucleotide or no overlap. Similarly, said first and said second AON preferably have less than 3 consecutive nucleotides sequence identity, more preferably less than 2 and preferably less than 1 nucleotide sequence identity. In a preferred embodiment said exon comprises at least two independent ESE sites. Said first AON is preferably targeted to at least two independent ESE sites and said second AON to a second thereof.

The qualification "sequence identity" as used herein preferably refers to identity using the nucleotides A, C, G or T, wherein T may be replaced by a U. In recent years, many different nucleotide analogues have been generated. Some of these have the same binding characteristics in kind and amount as the mentioned classic or natural nucleotides. However, most of them mimic the binding characteristics in kind but not in amount. In many cases the binding strength of an analogue to the complementary nucleotide is lower than that of the corresponding classical nucleotide. There are also analogues that mimic the binding characteristics of two or more of the classical nucleotides and there are also nucleotide analogues that are incorporated efficiently in a nucleic acid but that do not exhibit significant selectivity for, or binding to, a particular classic nucleotide on the opposing strand. A person skilled in the art is familiar with the particulars of these and similar analogues and can use them in an AON of the invention as long as the AON is capable of hybridising to the hybridisation site on the exon RNA.

An AON of the invention preferably comprises between 14-40 nucleotides or analogues thereof. Preferably said AON comprises between 14-25 nucleotides or analogues thereof. An AON of the invention preferably comprises less than 10% nucleotide analogues. An AON preferably comprises less than 4 nucleotide analogues, preferably less than 3, more preferably less than 2.

An AON of the invention is preferably a modified oligonucleotide. In a particularly preferred embodiment said AON comprises one or more 2'-O-methyl oligoribonucleotides, which render the AON resistant to RNase H induced degradation of DNA/RNA hybrids. Additionally, a phosphorothioate backbone can be used to increase the stability of AONs against nucleases and to enhance cellular uptake. An AON of the invention has in a preferred embodiment a full length phosphorothioate backbone and all bases (nucleotides) have a 2'-O-methyl modification. Alternatively, morpholino phosphorodiamidate DNA (morpholinos), locked nucleic acids (LNA) and ethylene bridged nucleic acids (ENA) oligos have been used to modulate splicing. An AON of the present invention can therefore also have these modifications. These modifications render the oligos RNase H and nuclease resistant and increase the affinity for the target RNA. For the ENA and LNA modification this increase is accompanied by a decreased sequence specificity.

An exon internal part of an exon, is a part that does not exhibit overlap with a 5'- or 3'-end of the exon. A 5'- and 3'-end of an exon contains the sequence information that is relevant for the joining region of the exon. An exon internal part of the exon is at least one and at least two and more preferably at least 5 nucleotides internal to the exon boundary. An exon internal AON may, in addition to the exon internal part as defined herein above, also have nucleotides that extend to the boundary of the exon or beyond. This is however, preferably not the case.

A method of the invention preferably further comprises including said first and said second AON in a set of AON when provision of said cell with said second AON increases the efficiency with which said exon is excluded from said mature mRNA in a cell that produces a precursor of said mRNA. Said set is subsequently preferably used to obtain exon skipping in target cells that express said pre-mRNA. The invention also provides a set comprising at least two AON wherein at least a first of said AON can hybridise to an exon internal part of an exon and a second of said AON can hybridise to another exon internal part of said exon. In a preferred embodiment of the invention said set is obtained by a method of the invention. In a particularly preferred embodiment said first and said second of said AON are targeted to ESE sites on said exon RNA. More preferably, said first and said second of said AON are targeted to independent ESE sites on said exon RNA.

A set of the invention can be used in many ways. In one embodiment said set is used to at least in part decrease the production of an aberrant protein in a cell. Such proteins can for instance be onco-proteins or viral proteins. In many tumors not only the presence of an onco-protein but also its relative level of expression have been associated to the phenotype of the tumor cell. Similarly, not only the presence of viral proteins but also the amount of viral protein in a cell determines the virulence of a particular virus. Moreover, for efficient multiplication and spread of a virus the timing of expression in the life cycle and the balance in the amount of certain viral proteins in a cell determines the whether viruses are efficiently or inefficiently produced. Using a set of the invention it is possible to lower the amount of aberrant protein in a cell such that for instance a tumor cell becomes less tumorigenic (metastatic) and/or a virus infected cell produces less virus.

In a preferred embodiment a set of the invention is used to convert said aberrant protein into a functional protein. In one embodiment said functional protein is capable of performing a function of a protein normally present in a cell but absent in the cells to be treated. Very often even partial restoration of function results in significantly improved performance of the cell thus treated. Due to the better performance, such cells can also have a selective advantage over unmodified cells thus aiding to the effectiveness of the treatment. This aspect of the invention is particularly suited for the restoration of expression of defective genes. This is achieved by causing the specific skipping of targeted exons, thus bypassing or correcting deleterious mutations (typically stop-mutations or frameshifting point mutations, single- or multi-exon deletions or insertions leading to translation termination).

Compared to gene-introduction strategies, exon skipping gene therapy requires the administration of much smaller therapeutic reagents, typically, but not limited to, AON comprising or mimicking between about 14-40 nucleotides. In a preferred embodiment AON of 14-25 nucleotides are used since these molecules are easier to produce and enter the cell more effectively. The set of the invention allows more flexibility in the subsequent design of effective and safe exon skipping strategies and/or administration systems. An important additional advantage of a gene function restoring set of AON is that it restores (at least some of) the activity of the endogenous gene, which still possesses most or all of its gene-regulatory circuitry, thus ensuring proper expression levels and the synthesis of tissue-specific isoforms.

This aspect of the invention can in principle be applied to any genetic disease or genetic predisposition to disease, in which targeted skipping of specific exons restores the translational reading frame when this has been disrupted by the original mutation. This application is particularly useful when translation of an internally slightly shorter or altered protein is fully or partly functional. Preferred embodiments for which this application can be of therapeutic value are: predisposition to second hit mutations in tumor suppressor genes, e.g. those involved in breast cancer, colon cancer, tuberous sclerosis, neurofibromatosis etc.,—where (partial) restoration of activity would preclude the manifestation of nullosomy by second hit mutations and thus would protect against tumorigenesis. Another preferred embodiment involves the (partial) restoration of defective gene products which have a direct disease causing effect, e.g., hemophilia A (clotting factor VIII deficiency, some forms of congenital hypothyroidism (due to thyroglobulin synthesis deficiency) and Duchenne Muscular Dystrophy (DMD), in which frameshifting deletions, duplications and stop mutations in the X-linked dystrophin gene cause severe, progressive muscle degradation. DMD is typically lethal in late adolescence or early adulthood, while non-frameshifting deletions or duplications in the same gene cause the much milder Becker muscular dystrophy (BMD), compatible with a life expectancy between 35-40 y to normal. In the embodiment as applied to DMD, the present invention enables exon skipping to extend an existing deletion (or alter the mRNA product of an existing duplication) by as many adjacent exons as required to restore the reading frame and generate an internally slightly shortened, but still functional protein. Based on the much milder clinical symptoms of BMD patients with the equivalent of this induced deletion, the disease in the DMD patients would have a much milder course after AON-therapy. Considering the many clinical uses of sets of the invention, a method of the invention preferably further comprises providing said set to a human cell. In one embodiment, the invention provides a set of AON obtainable by a method of the invention. In a preferred embodiment said set comprises at least one AON of table 1 or table 2. In a preferred embodiment the invention provides a set comprising at least AON of table 1 and/or table 2.

In a preferred aspect of this embodiment said set of at least two AON of table 1 and/or table 2 comprises h2AON1 and h2AON3, h43AON1 and h43AON2, h43AON1 and h43AON3, h43AON1 and h43AON4, h43AON1 and h43AON5, h43AON2 and h43AON5, h43AON3 and h43AON5, h43AON4 and h43AON5, h45AON1 and h45AON4, h45AON1 and h45AON5, h45AON1 and h45AON9, h45AON2 and h45AON3, h45AON2 and h45AON4, h45AON2 and h45AON5, h45AON3 and h45AON4, h45AON3 and h45AON5, h45AON3 and h45AON9, h45AON4 and h45AON5, h45AON5 and h45AON9, h46AON4 and h46AON8, h46AON4 and h46AON20, h46AON4 and h46AON22, h46AON6 and h46AON21, h46AON8 and h46AON22, h46AON8 and h46AON23, h46AON8 and h46AON26, h46AON9 and h46AON21, h46AON9 and h46AON22, h46AON9 and h46AON26, h46AON22 and h46AON24, h46AON24 and h46AON26, h47AON1 and h47AON3, h47AON1 and h47AON5, h47AON2 and h47AON3, h47AON2 and h47AON5, h47AON3 and h47AON4, h47AON3 and h47AON5, h47AON3 and h47AON6, h47AON4 and h47AON5, h47AON5 and h47AON6, h48AON1 and h48AON4, h48AON1 and h48AON6, h48AON1 and h48AON8, h48AON1 and h48AON9, h48AON1 and h48AON10, h48AON2 and h48AON10, h48AON3 and h48AON4, h48AON4 and h48AON6, h48AON6 and h48AON8, h48AON6 and h48AON9, h48AON6 and h48AON10, h48AON7 and h48AON9, h57AON1 and h57AON3 and/or h57AON2 and h57AON3. In a preferred embodiment said set of at least two AON of table 1 and/or table 2 comprises h43AON1 and h43AON3, h45AON1 and h45AON4, h45AON1 and h45AON5, h45AON1 and h45AON9, h45AON2 and h45AON3, h45AON2 and h45AON4, h45AON3 and h45AON4, h45AON3 and h45AON5, h45AON3 and h45AON9, h45AON4 and h45AON5, h45AON5 and h45AON9, h46AON9 and h46AON21, h47AON1 and h47AON3, h47AON1 and h47AON5, h47AON2 and h47AON3, h47AON2 and h47AON5, h47AON3 and h47AON4, h47AON3 and h47AON5, h47AON3 and h47AON6, h47AON4 and h47AON5, h47AON5 and h47AON6, h48AON1 and h48AON4, h48AON1 and h48AON8, h48AON3 and h48AON4, h57AON1 and h57AON3, h57AON2 and h57AON3. In a particularly preferred embodiment said set of at least two AON of table 1 and/or table 2 comprises h45AON1 and h45AON4, h45AON1 and h45AON5, h45AON1 and h45AON9, h45AON2 and h45AON3, h45AON3 and h45AON4, h45AON3 and h45AON5, h45AON3 and h45AON9, h4 AON4 and h45AON5, h45AON1 and h45AON9, h47AON1 and h47AON3, h47AON1 and h47AON5, h47AON2 and h47AON3, h47AON2 and h47AON5, h47AON3 and h47AON4, h47AON3 and h47AON5, h47AON3 and h47AON6, h47AON4 and h47AON5, h47AON5 and h47AON6, h57AON1 and h57AON3, h57AON2 and h57AON3. The present invention further provides an AON of table 2. Preferably, said AON of table 2 is h33AON1, h33AON2, h44AON3, h44AON4, h45AON11 or h52AON3.

In one aspect the invention further provides a method for the treatment of an individual suffering from a tumor, a virus infection and or a genetic disease and/or genetic predisposition, comprising administering a set of AON of the invention to said individual. The invention further provides a pharmaceutical composition comprising a set of AON according to the invention. Preferably said set is used for the treatment of an individual suffering from a tumor, a virus infection and or a genetic disease and/or genetic predisposition. Preferably, said set is used for the treatment of Duchenne Muscular Dystrophy (DMD).

The invention also provides a cell that produces an exon containing precursor of an mRNA, wherein said cell comprises a first AON that can hybridise to an exon internal part of said exon, and a second AON that can hybridise to another exon internal part of said exon.

EXAMPLES

Results and Discussion

Double-Targeting within One Exon

We hypothesized that by targeting multiple ESEs within one exon, skipping efficiencies might be increased for exons that could not be skipped at high levels using individual AONs. The relative locations of the AONs to putative ESEs (as predicted by ESEfinder) are depicted for each of these exons in FIG. 1A.

We first tested double targeting for 2 unskippable exons (exon 47 and 57). When human control myotube cultures were treated with different combinations of these AONs, significant levels of exon 47 and 57 skipping could be achieved as determined with RT-PCR analysis (FIGS. 1B and C, Supplementary Table 1). Interestingly, for exon 47 only combinations of non-overlapping AONs induced exon skipping, while those that do overlap were ineffective (Supplementary Table 1). Similarly, for exon 57 the combination of AONs that nearly overlap (h57AON1 and 2) did not induce exon skipping. This fits with our hypothesis that two mutually exclusive ESE sites are present in these exons.

For both exon 2 and exon 45 only a single AON reproducibly induced low levels of exon skipping (h2AON1 and h45AON5, respectively). Considerably higher levels of exon 45 skipping could be induced by combining the effective h45AON5 with ineffective AONs, as well as by combining two individually ineffective AONs (e.g. h45AON3 and h45AON9) (FIG. 1D). Thus for this exon two effective ESEs are likely to be present as well. In contrast, combinations of AONs did not increase skipping efficiencies for exon 2. In fact, combining the effective h2AON1 with the ineffective h2AON2 abolished exon 2 skipping (FIG. 1E). This interference was not observed for a combination of h2AON1 with h2AON3 (which overlaps less than h2AON2). For exons 43 and 48, effective AONs induced only moderate levels of skipping. For these exons the skipping levels could not be increased by using combinations of AONs (Supplementary Table 1). In these exons three or even more ESEs may be present. Therefore, we targeted exon 48 with a combination of 3 different AONs, which still did not improve skipping levels. Thus, it seems more likely that the splicing of this exon is largely independent of ESE sites. This is supported by the fact that the splice sites predicted are perfect (3' splice site) or near perfect (5' splice site) and that only a few ESEs are predicted for exon 48.

Finally, we used combinations of exon 46 specific AONs, some of which were already very efficient individually. We aimed to increase skipping levels to (near) 100%. However, none of the combinations used further improved skipping levels when compared to single targeting (Supplementary Table 1). This indicates that blocking one ESE site is sufficient to perturb the correct splicing of this exon. It is possible that the ESE sites of this exon are dependent on each other, so that by blocking one, more or all ESEs are inactivated. Alternatively, the secondary structure of the pre-mRNA may be changed upon AON binding so that the other ESE sites are no longer available for SR protein binding.

Interestingly, once more (partly) overlapping combinations appeared to negatively interfere with the individual exon skipping capacities, irrespective of whether the single AONs were effective or ineffective. It was expected that combinations of two ineffective, overlapping AONs would also be ineffective, since they either both target no functional ESE site or both target the same of two (or more) mutually exclusive ESE sites. For combinations of overlapping, effective AONs this finding was unexpected. It is possible, however, that these AONs compete with each other, and force one another to detach from the target transcript in a dynamic process, thereby making the target site available again for SR proteins. Upon binding SR proteins will recruit other splicing factors to the splice sites, and thus enhance exon inclusion rather than exon skipping.

Materials and Methods

AONs and Primers

All AONs used for the double targeting experiments were previously described (see Supplementary Table 1) ((11, 14, 15). All AONs contain 2-O-methyl RNA, phosphorothioate backbones and 5' fluorescein labels and were manufactured by Eurogentec (Belgium). (RT-) PCR primers were chosen in exons flanking the skipped exons (Eurogentec, Belgium; sequences available upon request).

Tissue Culturing, Transfection and RT-PCR Analysis

Control and DMD patient-derived myotube cultures were obtained as described previously (9, 22). For the exon skipping experiments, transfections were performed at least twice with 200 nM of each AON. In all experiments polyethylenimine (PEI, ExGen 500, MBI Fermentas) was used according to the manufacturer's instructions, with 2 to 3,5 µl PEI per µg AON. Depending on the number of effective AONs available for each of the targeted exons, different combinations of AONs were tested (Supplementary Table 1). Separate solutions of AON-PEI complexes were prepared for each AON. Transfection efficiencies were generally over 80% based on the presence of nuclear fluorescent signals. RNA was isolated 24-48 hours after transfection and RT-PCR analysis was performed as described previously (14). Successful transfection of each AON was confirmed by RT-PCR analysis with primers in the exons flanking the targeted exon(s). PCR fragments were isolated from the agarose gel and sequencing analysis was performed as described previously (10).

TABLE 1

Characteristics of used AONs

| AON | Sequence | SEQ ID NO: | Targeted exon | Skip[1] | ESEfinder values over threshold[2] | | | |
|---|---|---|---|---|---|---|---|---|
| | | | | | SF2/ASF[2] | SC35 | SRp40 | SRp55 |
| h2AON1[7] | cccauuuugugaauguuuucuuuu | 1. | 2 | ++ | 1.49 | 1.54 | 3.37 | 1.12 |
| h2AON2[7] | uugugcauuuacccauuuugug | 2. | 2 | − | 1.49 | 1.44 | 1.40 | 2.71 |
| h2AON3[7] | gaaaauugugcauuuacccauuuu | 3. | 2 | − | 1.59 | 1.44 | 1.40 | 2.71 |
| h8AON1 | cuuccuggauggcuucaau | 4. | 8 | ++ | 1.31 | 0.12 | 2.57 | 2.57 |
| h8AON3 | guacauuaagauggacuuc | 5. | 8 | ++ | −1.19 | 0.70 | 1.82 | 3.22 |
| h17AON1 | ccauuacaguugucuguguu | 6. | 17 | ++ | 3.77 | 2.92 | 3.04 | 2.91 |
| h17AON2 | uaaucugccucuucuuuugg | 7. | 17 | + | 1.76 | −0.68 | 3.83 | 1.54 |
| h19AON[7] | ucugcuggcaucuugc | 8. | 19 | + | 2.83 | 1.92 | 2.26 | 2.46 |
| h29AON1[7] | uauccucugaaugucgcauc | 9. | 29 | ++ | 5.74 | 1.07 | 4.60 | 3.53 |
| h29AON2[7] | gguuauccucugaaugucgc | 10. | 29 | ++ | 5.74 | 1.07 | 4.60 | 2.04 |
| h29AON4 | ccaucuguuagggucugug | 11. | 29 | ++ | 3.09 | 3.24 | 2.40 | 2.91 |
| h29AON6 | ucugugccaauaugcgaauc | 12. | 29 | ++ | 1.26 | 3.28 | 2.33 | 4.33 |
| h29AON9 | uuaaaugcucaaguucc | 13. | 29 | + | 1.83 | 1.41 | 1.09 | 1.39 |
| h29AON10 | guaguucccuccaacg | 14. | 29 | − | 1.61 | 0.79 | 1.66 | −0.11 |
| h29AON11 | cauguaguucccucc | 15. | 29 | + | 0.13 | 1.95 | 3.63 | 3.16 |
| h40AON1[7] | gagccuuuuucuucuuug | 16. | 40 | ++ | 1.31 | −0.39 | 1.44 | 0.77 |
| h40AON2[7] | uccuuucaucucugggcuc | 17. | 40 | ++ | 2.81 | 2.76 | 3.93 | 1.21 |
| h41AON1[7] | cuccucuuucuucuucugc | 18. | 41 | ++ | 3.82 | −0.39 | 1.53 | 0.93 |
| h41AON2[7] | cuucgaaacugagcaaauuu | 19. | 41 | + | 2.39 | 2.62 | 1.32 | 0.86 |
| h42AON1[7] | cuugugagacaugagug | 20. | 42 | + | 2.89 | 3.20 | 5.76 | 3.14 |
| h42AON2[7] | cagagacuccucuugcuu | 21. | 42 | + | 3.23 | 3.37 | 1.98 | 1.19 |
| h43AON1[7] | ugcugcugcuucuugcu | 22. | 43 | − | 1.83 | 1.47 | 3.61 | 2.83 |
| h43AON2[7] | uuguuaacuuuuucccauu | 23. | 43 | + | −0.78 | 1.06 | −0.24 | 0.10 |
| h43AON3 | uguuaaacuuuuucccauugg | 24. | 43 | − | 0.50 | 1.06 | 4.15 | 0.10 |
| h43AON4 | cauuuuguuaacuuuuuccc | 25. | 43 | − | −0.78 | 1.06 | 1.11 | 0.06 |
| h43AON5[8] | cguagcuucacccuuucc | 26. | 43 | ++ | 1.37 | 2.97 | 1.43 | 2.57 |
| h44AON1[7] | cgccgccauuucucaacag | 27. | 44 | ++ | 0.25 | 0.64 | 0.86 | 2.51 |
| h44AON2[7] | uuuguauuuagcauguuccc | 28. | 44 | ++ | −0.64 | 1.47 | 2.01 | 2.41 |
| h45AON1[7] | gcugaauuauuucuuccc | 29. | 45 | − | 1.79 | 1.01 | 3.07 | 2.41 |
| h45AON2[7] | uuuucugucugacagcug | 30. | 45 | − | 3.03 | 0.82 | 2.07 | 0.93 |
| h45AON3 | ucuguuuugaggauugc | 31. | 45 | − | 0.37 | 1.82 | 1.97 | 1.85 |
| h45AON4 | ccaccgcagauucaggc | 32. | 45 | − | 3.27 | 1.45 | 1.81 | 3.39 |
| h45AON5[8] | gcccaaugccauccugg | 33. | 45 | + | 0.50 | 2.30 | 1.19 | 0.35 |
| h45AON9[8] | uuugcagaccuccugcc | 34. | 45 | − | 3.96 | 3.20 | 0.86 | 2.56 |
| h46AON4[6] | cugcuuccuccaacc | 35. | 46 | + | 2.34 | 2.82 | 1.68 | 0.01 |
| h46AON6[6] | guuaucugcuuccuccaacc | 36. | 46 | + | 2.34 | 2.82 | 1.68 | 2.46 |
| h46AON8[6] | gcuuuucuuuuaguugcugc | 37. | 46 | ++ | −1.14 | 1.08 | 3.52 | 1.04 |
| h46AON9[6] | uuaguugcugcucuu | 38. | 46 | − | 0.66 | 1.30 | 0.51 | 2.83 |
| h46AON20 | gaaauucugacaagauauucu | 39. | 46 | + | 1.35 | 1.08 | 2.07 | 1.48 |
| h46AON21 | uaaaacaaauucauu | 40. | 46 | − | −2.28 | −0.40 | −0.72 | 0.83 |
| h46AON22 | uccagguucaaguggauac | 41. | 46 | ++ | 2.39 | 3.47 | 3.70 | 0.78 |
| h46AON23 | uuccagguucaagug | 42. | 46 | ++ | 1.61 | 1.03 | 1.47 | 0.78 |
| h46AON24 | ucaagcuuuucuuuuag | 43. | 46 | + | −1.19 | −1.09 | 3.52 | 0.18 |
| h46AON25 | cugacaagauauuccu | 44. | 46 | + | −0.80 | 1.08 | 0.74 | 1.48 |
| h46AON26 | agguucaaguggauacua | 45. | 46 | ++ | 2.39 | 3.47 | 3.70 | 2.09 |
| h47AON1[7] | ucuugcucuucggcuu | 46. | 47 | − | 3.82 | 1.55 | 3.68 | 1.21 |
| h47AON2[7] | cuugagcuuauuuucaaguuu | 47. | 47 | − | −0.89 | 2.17 | 2.20 | 0.53 |
| h47AON3 | uccaguucauuuaauuguuug | 48. | 47 | − | 1.70 | 0.22 | 2.76 | 1.02 |
| h47AON4 | cugcuugagcuuauuuucaaguu | 49. | 47 | − | 0.74 | 2.17 | 2.20 | 0.53 |
| h47AON5 | agcacuuacaagcacgggu | 50. | 47 | − | −1.37 | 2.05 | 1.25 | 2.07 |
| h47AON6 | uucaaguuuaucuugcucuuc | 51. | 47 | − | 1.11 | 0.96 | 0.74 | −0.40 |
| h48AON1[7] | uuucccuuguuucuc | 52. | 48 | − | 0.83 | 0.08 | 2.44 | 1.38 |
| h48AON2[7] | uuauaaauuuccaacugauuc | 53. | 48 | − | 0.64 | 1.50 | 2.33 | 1.31 |
| h48AON3 | ggucuuuauuugagcuuc | 54. | 48 | − | 0.01 | 1.72 | 2.83 | 1.58 |
| h48AON4 | cuucaagcuuuuuucaagcu | 55. | 48 | − | −1.34 | 1.32 | 2.32 | 0.42 |

TABLE 1-continued

Characteristics of used AONs

| | | | | | | | | |
|---|---|---|---|---|---|---|---|---|
| h48AON6 | gcuucaauuucuccuuguu | 56. | 48 | + | 0.83 | 0.34 | 1.62 | 2.57 |
| h48AON7 | uuuauuugagcuucaauuu | 57. | 48 | + | 0.01 | 1.72 | 1.62 | 2.57 |
| h48AON8 | gcugcccaaggucuuuu | 58. | 48 | − | 0.91 | 1.96 | 0.25 | 1.90 |
| h48AON9 | cuucaaggucuucaagcuuuu | 59. | 48 | + | 0.91 | 1.96 | 2.32 | 2.21 |
| h48AON10 | uaacugcucuucaaggucuuc | 60. | 48 | + | 0.91 | 1.96 | 2.32 | 2.21 |
| h49AON1[7] | cuuccacauccgguuguuu | 61. | 49 | ++ | 3.02 | 0.52 | 1.96 | 3.41 |
| h49AON2[7] | guggcugguuuuuccuugu | 62. | 49 | ++ | 0.56 | 0.05 | 0.70 | 1.38 |
| h50AON1[7] | cucagagcucagaucuu | 63. | 50 | ++ | 1.69 | 3.02 | 2.71 | −0.03 |
| h50AON2[7] | ggcugcuuugcccuc | 64. | 50 | + | 1.10 | 1.37 | 1.41 | 2.83 |
| h51AON1[7] | ucaaggaagauggcauuucu | 65. | 51 | ++ | −0.31 | 1.48 | 1.35 | 0.41 |
| h51AON24 | gaaagccagucgguaaguuc | 66. | 51 | − | 1.77 | 1.14 | 4.90 | 2.04 |
| h51AON27 | cacccaccaucaccc | 67. | 51 | − | 0.39 | 1.74 | 0.38 | 1.31 |
| h51AON2[7] | ccucugugauuuuauaacuugau | 68. | 51 | ++ | 2.68 | 2.27 | 3.94 | 2.91 |
| h51AON29 | ugauauccucaaggucaccc | 69. | 51 | ++ | 1.67 | 1.91 | 2.88 | 2.82 |
| h52AON1 | uugcuggucuuguuuuc | 70. | 52 | + | 1.56 | 3.61 | 2.44 | 0.52 |
| h52AON2 | ccguaaugauuguucu | 71. | 52 | − | −0.07 | 1.11 | 2.28 | −0.80 |
| h53AON1[7] | cuguugccuccgguucug | 72. | 53 | + | 3.08 | 2.26 | 1.63 | 0.77 |
| h53AON2[7] | uuggcucuggccuguccu | 73. | 53 | − | 2.20 | 4.04 | 3.40 | 0.21 |
| h54AON1 | uacauuugucugccacugg | 74. | 54 | ++ | 3.77 | 1.64 | 4.00 | 1.88 |
| h54AON2 | cccggagaaguuucaggg | 75. | 54 | ++ | 3.14 | 1.80 | 3.54 | 1.34 |
| h55AON1 | cuguugcaguaaucuaugag | 76. | 55 | + | 0.74 | 4.82 | 4.92 | 2.92 |
| h55AON2 | ugccauuguuucaucagcucuuu | 77. | 55 | + | 2.70 | 2.29 | 3.46 | 1.27 |
| h55AON3 | ugcaguaaucuaugaguuuc | 78. | 55 | + | 0.74 | 4.82 | 4.92 | 2.41 |
| h55AON5 | uccuguaggacauuggcagu | 79. | 55 | ++ | 3.03 | 2.67 | 5.66 | 2.34 |
| h55AON6 | gagucuucuaggagccuu | 80. | 55 | ++ | 0.87 | 5.77 | 3.36 | 0.33 |
| h56AON1 | uuuuuggcuguuuucaucc | 81. | 56 | + | 2.77 | 1.56 | 2.52 | 2.22 |
| h56AON2 | guucacuccacuugaaguuc | 82. | 56 | − | 0.78 | 1.88 | 4.04 | 1.52 |
| h56AON3 | ccuuccagggaucucagg | 83. | 56 | + | 1.81 | 5.52 | 3.68 | 0.27 |
| h57AON1 | uaggugccugccggcuu | 84. | 57 | − | 2.11 | 3.30 | 2.54 | 2.03 |
| h57AON2 | cugaacugcuggaaagucgcc | 85. | 57 | − | 2.47 | 1.95 | 2.77 | 2.41 |
| h57AON3 | uucagcuguagccacacc | 86. | 57 | − | 2.83 | 4.73 | 4.81 | 4.10 |
| h58AON1 | uucuuuaguuuucaauuccuc | 87. | 58 | − | 0.63 | 1.70 | 2.52 | 1.60 |
| h58AON2 | gaguuucucuaguccuucc | 88. | 58 | + | 1.65 | 3.45 | 2.18 | 0.68 |
| h59AON1 | caauuuuucccacucaguauu | 89. | 59 | − | 1.77 | 0.34 | 3.53 | 2.23 |
| h59AON2 | uugaaguuccuggagucuu | 90. | 59 | ++ | 1.31 | 4.84 | 3.26 | 1.34 |
| h60AON1 | guucucuuucagaggcgc | 91. | 60 | + | 0.66 | 3.66 | 2.29 | 3.00 |
| h60AON2 | gugcugagguuauacggug | 92. | 60 | − | 2.87 | 2.56 | 4.08 | 2.78 |
| h61AON1 | gucccuguggggcuucaug | 93. | 61 | − | 5.26 | 2.92 | 5.97 | 2.57 |
| h61AON2 | gugcugagaugcuggacc | 94. | 61 | + | 2.28 | 3.32 | 4.43 | 3.64 |
| h62AON1 | uggcucucucccaggg | 95. | 62 | ++ | 1.08 | 0.33 | 1.89 | −0.50 |
| h62AON2 | gggcacuuuguuuggcg | 96. | 62 | − | 1.70 | 0.56 | 1.71 | 0.09 |
| h63AON1 | ggucccagcaaguuguuug | 97. | 63 | + | 1.70 | 0.97 | 3.16 | 1.25 |
| h63AON2 | guagagcucugucauuuuggg | 98. | 63 | + | 2.81 | 2.57 | 3.12 | 0.93 |
| h71AON1 | gccagaaguugaucagagu | 99. | 71 | ++ | 0.12 | 3.35 | 4.36 | 1.47 |
| h71AON2 | ucuacuggccagaaguug | 100. | 71 | ++ | 1.37 | 4.61 | 4.36 | 1.47 |
| h72AON1 | ugaguaucaucgugugaaag | 101. | 72 | ++ | 6.59 | 0.60 | 6.02 | 0.25 |
| h72AON2 | gcauaauguucaaugcgug | 102. | 72 | + | 0.77 | 2.43 | 1.26 | 2.14 |
| h73AON1 | gauccauugcuguuuucc | 103. | 73 | ++ | 1.22 | 0.89 | 2.16 | 2.47 |
| h73AON2 | gagaugcuaucauuuagauaa | 104. | 73 | + | −0.48 | 0.68 | 2.28 | 3.64 |
| h74AON1 | cuggcucaggggggagu | 105. | 74 | ++ | 1.35 | 2.39 | 2.35 | 1.39 |
| h74AON2 | uccccucuuuccucacucu | 106. | 74 | + | 3.04 | 0.33 | 1.68 | 2.82 |
| h75AON1 | ccuuuauguucgugcugcu | 107. | 75 | ++ | 3.64 | 1.41 | 3.39 | 2.83 |
| h75AON2 | ggcggccuuuguguugac | 108. | 75 | ++ | 1.51 | 1.11 | 3.71 | 1.12 |
| h76AON1 | gagagguagaaggagagga | 109. | 76 | − | 0.08 | 1.28 | 3.53 | 3.22 |
| h76AON2 | auaggcugacugcugucgg | 110. | 76 | + | 3.23 | 1.47 | 4.30 | 1.58 |
| h77AON1 | uuguguccuggggagga | 111. | 77 | ++ | 4.26 | 3.50 | 3.57 | −0.18 |

TABLE 1-continued

Characteristics of used AONs

| | | | | | | | | |
|---|---|---|---|---|---|---|---|---|
| h77AON2 | ugcuccaucaccuccucu | 112. | 77 | ++ | 2.43 | 0.32 | -0.21 | 1.65 |
| h78AON1 | gcuuuccaggggurauuuc | 113. | 78 | ++ | 1.81 | 4.04 | 3.32 | 0.62 |
| h78AON2 | cauuggcuuuccagggg | 114. | 78 | ++ | 1.81 | 2.95 | 3.32 | 0.27 |

| AON | Sequence | SEQ ID NO: | Distance from[3] 3' SS[3] | 5' SS | Length | Fraction open[4] | % GC |
|---|---|---|---|---|---|---|---|
| h2AON1[7] | cccauuuugugaauguuuucuuuu | 1. | 19 | 21 | 24 | 0.29 | 29% |
| h2AON2[7] | uugugcauuuacccauuuugug | 2. | 32 | 10 | 22 | 0.32 | 36% |
| h2AON3[7] | gaaaauugugcauuuacccauuuu | 3. | 35 | 5 | 24 | 0.29 | 29% |
| h8AON1 | cuuccuggauggcuucaau | 4. | 26 | 139 | 19 | 0.53 | 47% |
| h8AON3 | guacauuaagauggacuuc | 5. | 84 | 81 | 19 | 0.53 | 37% |
| h17AON1 | ccauuacaguugucugugu | 6. | 36 | 122 | 20 | 0.40 | 40% |
| h17AON2 | uaaucugccucuucuuuugg | 7. | 132 | 26 | 20 | 0.60 | 40% |
| h19AON[7] | ucugcuggcaucuugc | 8. | 39 | 35 | 16 | 0.56 | 56% |
| h29AON1[7] | uauccucugaaugucgcauc | 9. | 15 | 117 | 20 | 0.30 | 45% |
| h29AON2[7] | gguuauccucugaaugucgc | 10. | 18 | 114 | 20 | 0.40 | 50% |
| h29AON4 | ccaucuguuagggucugug | 11. | 59 | 74 | 19 | 0.58 | 53% |
| h29AON6 | ucugugccaauaugcgaauc | 12. | 45 | 87 | 20 | 0.55 | 45% |
| h29AON9 | uuaaaugucucsaguucc | 13. | 105 | 29 | 18 | 0.28 | 33% |
| h29AON10 | guaguucccuccaacg | 14. | 127 | 9 | 16 | 0.44 | 56% |
| h29AON11 | cauguaguucccucc | 15. | 131 | 6 | 15 | 0.67 | 53% |
| h40AON1[7] | gagccuuuuucuucuuug | 16. | 13 | 123 | 19 | 0.58 | 37% |
| h40AON2[7] | uccuuucaucucugggcuc | 17. | 127 | 9 | 19 | 0.47 | 53% |
| h41AON1[7] | cuccucuuucuucuucugc | 18. | 18 | 148 | 19 | 0.74 | 47% |
| h41AON2[7] | cuucgaaacugagcaaauuu | 19. | 145 | 20 | 20 | 0.50 | 35% |
| h42AON1[7] | cuugugagacaugagug | 20. | 90 | 90 | 17 | 0.47 | 47% |
| h42AON2[7] | cagagacucccuugcuu | 21. | 175 | 4 | 18 | 0.00 | 50% |
| h43AON1[7] | ugcugcugucuucuugcu | 22. | 52 | 105 | 18 | 0.39 | 50% |
| h43AON2[7] | uuguuaacuuuuucccauu | 23. | 134 | 22 | 19 | 0.63 | 26% |
| h43AON3 | uguuaacuuuuucccauugg | 24. | 132 | 23 | 20 | 0.55 | 35% |
| h43AON4 | cauuuuguuaacuuuuuccc | 25. | 137 | 18 | 20 | 0.45 | 30% |
| h43AON5[8] | cuguagcuucacccuuucc | 26. | 90 | 66 | 19 | 0.37 | 53% |
| h44AON1[7] | cgccgccauuucucaacag | 27. | 15 | 116 | 19 | 0.26 | 58% |
| h44AON2[7] | uuuguauuuagcauguuccc | 28. | 87 | 43 | 20 | 0.40 | 35% |
| h45AON1[7] | gcugaauuauuucuucccc | 29. | 58 | 101 | 19 | 0.37 | 42% |
| h45AON2[7] | uuuuucugucugacagcug | 30. | 154 | 5 | 19 | 0.74 | 42% |
| h45AON3 | ucuguuuugaggauugc | 31. | 75 | 85 | 18 | 0.39 | 39% |
| h45AON4 | ccaccgcagauucaggc | 32. | 122 | 39 | 17 | 0.47 | 65% |
| h45AON5[8] | gcccaaugccaucugg | 33. | 6 | 155 | 17 | 0.29 | 65% |
| h45AON9[8] | uuugcagaccuccugcc | 34. | 137 | 24 | 17 | 0.65 | 59% |
| h46AON4[6] | cugcuuccuccaacc | 35. | 63 | 72 | 15 | 0.07 | 60% |
| h46AON6[6] | guuaucugcuuccuccaacc | 36. | 63 | 67 | 20 | 0.15 | 50% |
| h46AON8[6] | gcuuuucuuuuaguugcugc | 37. | 115 | 15 | 20 | 0.60 | 40% |
| h46AON9[6] | uuaguugcugcucuu | 38. | 111 | 24 | 15 | 1.00 | 40% |
| h46AON20 | gaaauucugacaagauauucu | 39. | 15 | 114 | 21 | 0.48 | 29% |
| h46AON21 | uaaaacaaauucauu | 40. | 47 | 88 | 15 | 0.40 | 13% |
| h46AON22 | uccagguucaagugggauac | 41. | 90 | 40 | 20 | 0.60 | 50% |
| h46AON23 | uuccagguucaagug | 42. | 96 | 39 | 15 | 0.53 | 47% |
| h46AON24 | ucaagcuuuucuuuuag | 43. | 122 | 11 | 17 | 0.35 | 29% |
| h46AON25 | cugacaagauauucuu | 44. | 14 | 120 | 16 | 0.88 | 31% |
| h46AON26 | agguucaagugggauacua | 45. | 88 | 43 | 19 | 0.79 | 42% |
| h47AON1[7] | ucuugcucuucgggcuu | 46. | 87 | 47 | 18 | 0.22 | 50% |
| h47AON2[7] | cuugagcuuauuuucaaguuu | 47. | 101 | 30 | 21 | 0.48 | 29% |
| h47AON3 | uccaguuucauuuaauuguuu | 48. | 39 | 91 | 22 | 0.45 | 27% |
| h47AON4 | cugcuugagcuuauuuucaaguu | 49. | 103 | 26 | 23 | 0.39 | 35% |
| h47AON5 | agcacuuacaagcacgggu | 50. | 63 | 70 | 19 | 0.53 | 53% |
| h47AON6 | uucaaguuuaucuugcucuuc | 51. | 94 | 37 | 21 | 0.33 | 33% |
| h48AON1[7] | uuucuccuuguuucuc | 52. | 19 | 153 | 16 | 0.81 | 38% |
| h48AON2[7] | uuauaaauuuccaacugauuc | 53. | 133 | 34 | 21 | 0.48 | 24% |
| h48AON3 | ggucuuuuauuuagcuuc | 54. | 37 | 132 | 19 | 0.74 | 37% |
| h48AON4 | cuucaagcuuuuuuucaagcu | 55. | 62 | 105 | 21 | 0.62 | 33% |

TABLE 1-continued

Characteristics of used AONs

| | | | | | | | |
|---|---|---|---|---|---|---|---|
| h48AON6 | gcuucaauuucuccuuguu | 56. | 23 | 146 | 19 | 0.63 | 37% |
| h48AON7 | uuuauuugagcuucaauuu | 57. | 32 | 137 | 19 | 0.68 | 21% |
| h48AON8 | gcugcccaaggucuuuu | 58. | 48 | 123 | 17 | 0.53 | 53% |
| h48AON9 | cuucaaggucuucaagcuuuu | 59. | 71 | 96 | 21 | 0.62 | 38% |
| h48AON10 | uaacugcucuucaaggucuuc | 60. | 79 | 88 | 21 | 0.48 | 43% |
| h49AON1[7] | cuuccacauccgguuguuu | 61. | 25 | 60 | 19 | 0.42 | 47% |
| h49AON2[7] | guggcugguuuuuccuugu | 62. | 60 | 25 | 19 | 0.32 | 47% |
| h50AON1[7] | cucagagcucagaucuu | 63. | 11 | 83 | 17 | 0.24 | 47% |
| h50AON2[7] | ggcugcuuugcccuc | 64. | 60 | 36 | 15 | 0.47 | 67% |
| h51AON1[7] | ucaaggaagauggcauuucu | 65. | 68 | 147 | 20 | 0.70 | 40% |
| h51AON24 | gaaagccagucgguaaguuc | 66. | 132 | 83 | 20 | 0.80 | 50% |
| h51AON27 | cacccaccaucaccc | 67. | 181 | 39 | 15 | 0.00 | 67% |
| h51AON2[7] | ccucugugauuuuauaacuugau | 68. | 160 | 52 | 23 | 0.22 | 30% |
| h51AON29 | ugauauccucaaggucaccc | 69. | 191 | 24 | 20 | 0.25 | 50% |
| h52AON1 | uugcggucuuuguuuuc | 70. | 69 | 33 | 18 | 0.50 | 39% |
| h52AON2 | ccguaaugauuguucu | 71. | 97 | 7 | 16 | 0.25 | 38% |
| h53AON1[7] | cguugccuccgguucug | 72. | 45 | 151 | 18 | 0.78 | 61% |
| h53AON2[7] | uuggcucuggccuguccu | 73. | 128 | 68 | 18 | 0.50 | 61% |
| h54AON1 | uacauuugucugccacugg | 74. | 21 | 118 | 18 | 0.56 | 50% |
| h54AON2 | cccggagaaguuucaggg | 75. | 58 | 80 | 19 | 0.58 | 58% |
| h55AON1 | cguuugcaguaaucuaugag | 76. | 33 | 139 | 20 | 0.65 | 40% |
| h55AON2 | ugccauuguuucaucagcucuuu | 77. | 167 | 2 | 23 | 0.52 | 39% |
| h55AON3 | ugcaguaaucuaugaguuuc | 78. | 29 | 143 | 20 | 0.60 | 35% |
| h55AON5 | uccguaggacauuggcagu | 79. | 104 | 68 | 20 | 0.35 | 50% |
| h55AON6 | gagucuucuaggagccuu | 80. | 139 | 35 | 18 | 0.28 | 50% |
| h56AON1 | uuuuuggcuguuuucaucc | 81. | 48 | 107 | 20 | 0.55 | 35% |
| h56AON2 | guucacuccacuugaaguuc | 82. | 129 | 26 | 20 | 0.35 | 45% |
| h56AON3 | ccuuccagggaucucagg | 83. | 69 | 88 | 18 | 0.56 | 61% |
| h57AON1 | uaggugccugccggcuu | 84. | 97 | 45 | 17 | 0.41 | 65% |
| h57AON2 | cugaacugcuggaaagucgcc | 85. | 118 | 20 | 21 | 0.57 | 57% |
| h57AON3 | uucagcuguagccacacc | 86. | 64 | 77 | 18 | 0.28 | 56% |
| h58AON1 | uucuuuaguuuucaauuccuc | 87. | 9 | 92 | 22 | 0.64 | 32% |
| h58AON2 | gaguuucucuaguccuucc | 88. | 86 | 18 | 19 | 0.37 | 47% |
| h59AON1 | caauuuuucccacucaguauu | 89. | 66 | 184 | 21 | 0.57 | 33% |
| h59AON2 | uugaaguuccuggagucuu | 90. | 134 | 118 | 19 | 0.47 | 42% |
| h60AON1 | guucucuuucagaggcgc | 91. | 19 | 112 | 18 | 0.56 | 56% |
| h60AON2 | gugcugagguuauacggug | 92. | 92 | 38 | 19 | 0.84 | 53% |
| h61AON1 | gucccuguggcuucaug | 93. | 31 | 31 | 19 | 0.37 | 58% |
| h61AON2 | gugcugagaugcuggacc | 94. | 51 | 12 | 18 | 0.56 | 61% |
| h62AON1 | uggcucucucccaggg | 95. | 15 | 32 | 16 | 0.50 | 69% |
| h62AON2 | gggcacuuuguuuggcg | 96. | 37 | 9 | 17 | 0.47 | 59% |
| h63AON1 | ggucccagcaaguuguuu | 97. | 11 | 34 | 19 | 0.79 | 53% |
| h63AON2 | guagagcucugucauuuuggg | 98. | 33 | 10 | 21 | 0.38 | 48% |
| h71AON1 | gccagaaguugaucagagu | 99. | 8 | 14 | 19 | 0.79 | 47% |
| h71AON2 | ucuacuggccagaaguug | 100. | 16 | 7 | 18 | 0.50 | 50% |
| h72AON1 | ugaguaucaucgugugaaag | 101. | 20 | 28 | 20 | 0.60 | 40% |
| h72AON2 | gcauaauguucaaugcgug | 102. | 42 | 7 | 19 | 0.47 | 42% |
| h73AON1 | gauccauugcuguuuucc | 103. | 13 | 37 | 18 | 0.39 | 44% |
| h73AON2 | gagaugcuaucauuuagauaa | 104. | 31 | 16 | 21 | 0.29 | 29% |
| h74AON1 | cuggcucaggggggagu | 105. | 51 | 93 | 17 | 0.59 | 71% |
| h74AON2 | uccccucuuuccucacucu | 106. | 72 | 70 | 19 | 0.16 | 53% |
| h75AON1 | ccuuuauguucgugcugcu | 107. | 33 | 194 | 19 | 0.21 | 47% |
| h75AON2 | ggcggccuuuguguugac | 108. | 144 | 84 | 18 | 0.39 | 61% |
| h76AON1 | gagagguagaaggagagga | 109. | 37 | 70 | 19 | 0.32 | 53% |
| h76AON2 | auaggcugacugcugucgg | 110. | 65 | 42 | 19 | 0.32 | 58% |
| h77AON1 | uuguguccuggggagga | 111. | 20 | 58 | 17 | 0.47 | 59% |

TABLE 1-continued

Characteristics of used AONs

| | | | | | | | |
|---|---|---|---|---|---|---|---|
| h77AON2 | ugcuccaucaccuccucu | 112. | 47 | 30 | 18 | 0.39 | 56% |
| h78AON1 | gcuuuccaggggu auuuc | 113. | 4 | 12 | 18 | 0.78 | 50% |
| h78AON2 | cauuggcuuuccagggg | 114. | 10 | 7 | 17 | 0.71 | 59% |

[1]++ Exon skipping observed in over 25% of transcripts in normal control myotube cultures; + exon skipping observed in up to 25% of transcripts; − no exon skipping detected
[2]For each AON the highest value is gives for each of the SR proteins
[3]Number of nucleotides between the AONs and the 5' and 3' splice sites (SS) in nucleotides. The distance to the 3' and 5' splice sites is determined from the first (3' splice site) or last (5' splice site) nucleotide in the target sequence
[4]The fraction of available nucleotides targeted by the AON in the predicted secondary RNA structure over the total length of the AON
[5]This AON targets part of the ESE deleted in the deletion Kobe (Matsuo et al., 1990; Matsuo et al., 1991)
[6]Previously published (van Deutekom et al., 2001)
[7]Previously published (Aartsma-Rus et al., 2002)
[8]Previously published (van Deutekom et al., 2001; Aartsma-Rus et al., 2003; Aartsma-Rus et al., 2004)

TABLE 2

| AON name | Targeted Human Dystrophin Exon | Sequence | SEQ ID NO: | Effective |
|---|---|---|---|---|
| h33AON1 | 33 | cugacguccagucuuuauc | (SEQ ID NO: 115) | yes |
| h33AON2 | 33 | gggauuuuccgucugcuu | (SEQ ID NO: 116) | yes |
| h44AON3 | 44 | ccgccauuucucaacag | (SEQ ID NO: 117) | yes |
| h44AON4 | 44 | uucucaggaauuugugucuuu | (SEQ ID NO: 118) | yes |
| h45AON10 | 45 | caguuugccgcugccca | (SEQ ID NO: 119) | no |
| h45AON11 | 45 | guugcauucaauguucugac | (SEQ ID NO: 120) | yes |
| h45AON12 | 45 | auuuuccuguagaauacugg | (SEQ ID NO: 121) | no |
| h52AON3 | 52 | gcuggucuuguuuuucaa | (SEQ ID NO: 122) | yes |
| h52AON4 | 52 | uggucuuguuuuucaaauuu | (SEQ ID NO: 123) | no |
| h52AON5 | 52 | gucuuguuuuucaaauuuug | (SEQ ID NO: 124) | no |
| h52AON6 | 52 | cuuguuuuucaaauuuuggg | (SEQ ID NO: 125) | no |
| h52AON7 | 52 | uguuuuucaaauuuuggc | (SEQ ID NO: 126) | no |
| h64AON1 | 64 | uccauaaagcugagaaucug | (SEQ ID NO: 127) | no |
| h64AON2 | 64 | gccuucugcagucuucgg | (SEQ ID NO: 128) | no |

SUPPLEMENTARY TABLE 1

Overview of the AONs used and results obtained for the double targeting experiments

| Target Exon | AON | Result 1 | Combined with (Result)[2] | | | | | | | |
|---|---|---|---|---|---|---|---|---|---|---|
| 2 | h2AON1 | + | AON2(−) | AON3(−) | | | | | | |
| | h2AON2 | − | | AON3(−) | | | | | | |
| | h2AON3 | − | | | | | | | | |
| 43 | h43AON1 | − | AON2(−) | AON3(+) | AON4(−) | AON5(−) | | | | |
| | h43AON2 | + | | | | AON5(−) | | | | |
| | h43AON3 | − | | | | AON5(−) | | | | |
| | h43AON4 | − | | | | AON5(−) | | | | |
| | h43AON5 | + | | | | | | | | |
| 45 | h45AON1 | − | AON2(−) | | AON4(−) | AON5(−) | AON9(−) | | | |
| | h45AON2 | − | | AON3(−) | AON4(+) | AON5(−) | AON9(−) | | | |
| | h45AON3 | − | | | AON4(−) | AON5(−) | AON9(−) | | | |
| | h45AON4 | + | | | | AON5(+) | AON9(−) | | | |
| | h45AON5 | − | | | | | | | | |
| | h45AON9 | − | | | | | | | | |
| 46 | h46AON4 | + | AON6(−) | AON8(−) | | AON20(−) | AON21(−) | AON22(−) | | AON25(−) |
| | h46AON6 | + | | | | | AON21 (−) | | AON24 (−) | |
| | h46AON8 | + | | | | | | AON22 (−) | AON23 (−) | AON26 (−) |
| | h46AON9 | − | | | | | AON21 (−) | AON22 (−) | AON23 (−) | AON26 (−) |
| | h46AON20 | + | | | | | | | | |
| | h46AON21 | − | | | | | | | | |
| | h46AON22 | + | | | | | | | AON24(−) | |
| | h46AON23 | + | | | | | | | AON24(−) | |

SUPPLEMENTARY TABLE 1-continued

Overview of the AONs used and results obtained for the double targeting experiments

| | | | | | | | | | | | | |
|---|---|---|---|---|---|---|---|---|---|---|---|---|
| | h46AON 24 | + | | | | | | | | | | AON26 (=) |
| | h46AON 25 | + | | | | | | | | | | |
| | h46AON 26 | + | | | | | | | | | | |
| 47 | h47AON1 | - | AON2(-) | AON3(=) | AON4(-) | AON5(=) | | | | | | |
| | h47AON2 | - | | AON3(=) | | AON5(=) | | | | | | |
| | h47AON3 | - | | | AON4(=) | AON5(=) | AON6(=) | | | | | |
| | h47AON4 | - | | | | AON5(+) | AON6(=) | | | | | |
| | h47AON5 | - | | | | | | | | | | |
| | h47AON6 | - | | | | | | | | | | |
| 48 | h48AON1 | - | AON2(-) | AON3(-) | AON4(=) | AON6(=) | | AON8(+) | AON9(=) | AON10(=) | | |
| | h48AON2 | | | AON3(-) | AON4(=) | AON6(-) | AON7(-) | | | AON10(=) | | |
| | h48AON3 | - | | | | AON6(=) | AON7(-) | | | | | |
| | h48AON4 | - | | | | | | | | | | |
| | h48AON6 | + | | | | | | AON8(=) | AON9(=) | AON10(=) | | |
| | h48AON7 | + | | | | | | | AON9(=) | AON10(-) | AON10(-) | |
| | h48AON8 | - | | | | | | | | | | |
| | h48AON9 | + | | | | | | | | | | |
| | h48AON 10 | + | | | | | | | | | | |
| 57 | h57AON1 | - | AON2(-) | AON3(=) | | | | | | | | |
| | h57AON2 | - | | AON3(=) | | | | | | | | |
| | h57AON3 | - | | | | | | | | | | |

[1]"+" exon skipping observed for this individual AON,
"-" exon skipping not (reproducibly) observed for this individual AON
[2]Results of the double targeting compared to the single targeting;
"+" double targeting more efficient than targeting with either of the single AONs,
"=" efficiency double targeting comparable to most efficient single AON,
"-" double targeting not effective or less efficient than most efficient single AON.
Effective AONs are shaded light grey, combinations that work notably better than the most efficient single AON, are shaded in darker grey, combinations that overlap are underlined.

Figure 1A:
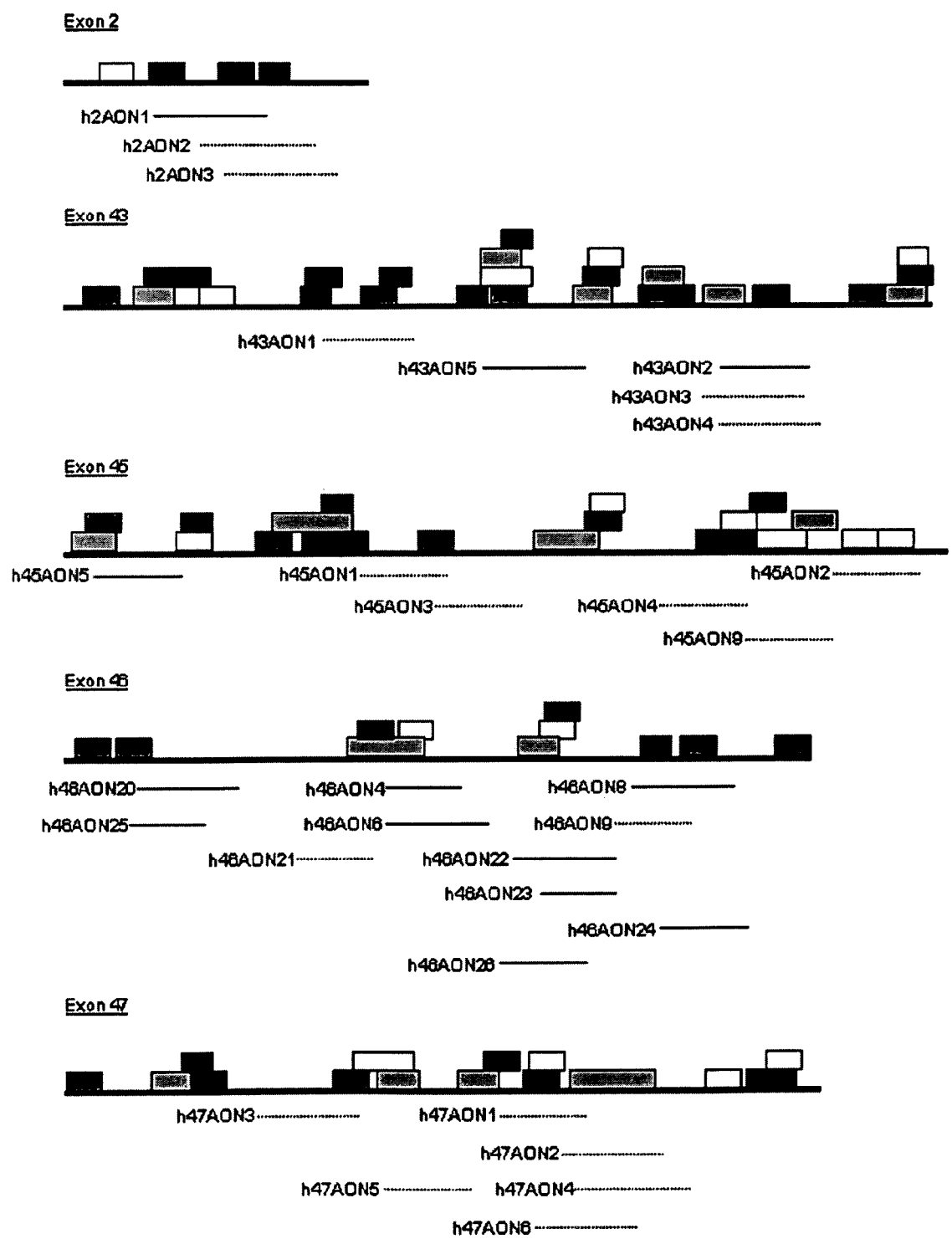
FIG. 1. Double targeting. (A). Relative locations of AONs and putative ESE sites within exons 2, 43, 45-48 and 57. Exons and AONs are drawn to scale as lines for each exon. Putative binding sites of SF2/ASF, SC35, SRp40 and SRp55 as predicted by ESEfinder are depicted as boxes at their respective locations. (B-E). Some examples of RT-PCR analysis after double targeting experiments. (B and C). For exons 47 and 57 none of the available AONs reproducibly induced exon skipping. Using combinations of these AONs, however, exon 47 and 57 skipping was reproducibly induced at significant levels. For exon 57 combinations containing h57AON3 were most efficient, while for exon 47 all non-overlapping combinations induced comparable levels of exon 47 skipping. In some cases an additional band could be observed in the exon 47 PCR, which was slightly shorter than the wild type product. This band was not reproducible, was observed both in treated and non-treated samples, and appeared to be an a-specific PCR product containing DMD exons 72-74. (D). For exon 45 only one of the available AONs reproducibly induced skipping, albeit at low levels (h45AON5). Very low levels of exon skipping were occasionally observed for h45AON1 and h45AON4, but this was not reproducible. Exon 45 skipping could be achieved at much higher levels using combinations of AONs. The highest levels of exon 45 skipping were observed for combinations of h45AON5 and h45AON1 or h45AON3 and for h45AON1 and h45AON9. In contrast, a mixture of the overlapping h45AON2 and h45AON9 was ineffective. (E). For exon 2 only overlapping AONs were available. When the effective h2AON1 was combined with the ineffective, overlapping h2AON2, no skipping could be induced. This effect was not seen when h2AON1 was combined with the ineffective, less overlapping h2AON3. The sequence of the mentioned AON is given in article Aartsma-Rus A, et al. (2005). Functional analysis of 114 exon-internal AONs for targeted DMD exon skipping: indication for steric hindrance of SR protein binding sites. Oligonucleotides 15: 284-297.
Figure 1B:
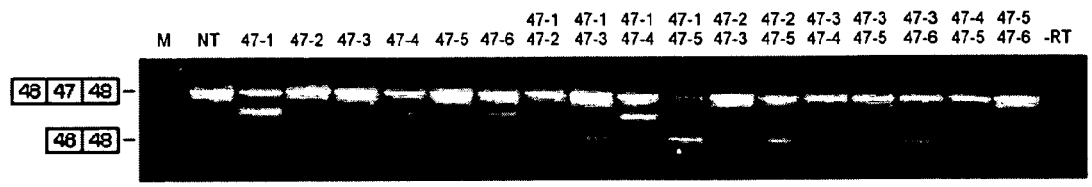
Figure 1C:
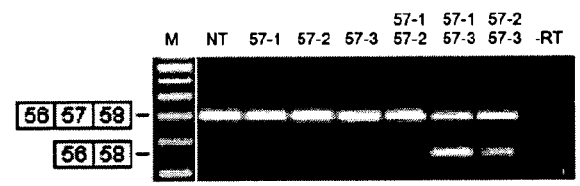
Figure 1D:
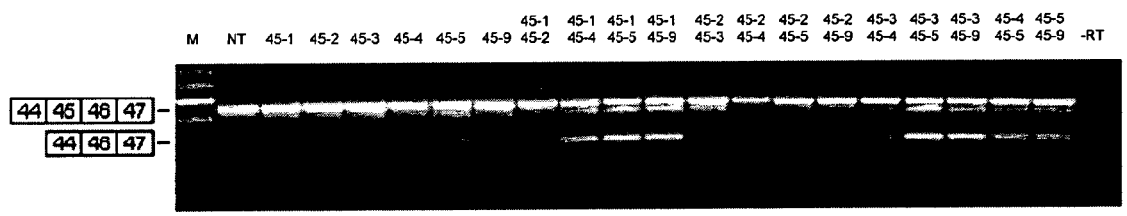
Figure 1E:
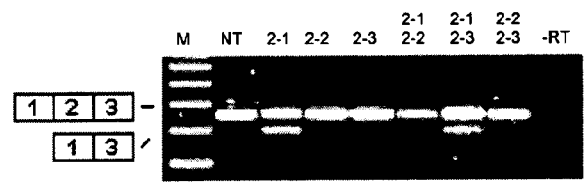

NT is non transfected, -RT is negative control, M is 100 bp size marker.

LITERATURE CITED

1. Emery A E. (2002). The muscular dystrophies. Lancet 359: 687-95.
2. Monaco A P, Bertelson C J, Liechti-Gallati S, Moser H, and Kunkel LM. (1988). An explanation for the phenotypic differences between patients bearing partial deletions of the DMD locus. Genomics 2: 90-95.
3. Hoffman E P, et al. (1988). Characterization of dystrophin in muscle-biopsy specimens from patients with Duchenne's or Becker's muscular dystrophy. N Engl J Med 318: 1363-1368.
4. Koenig M, Hoffman E P, Bertelson C J, Monaco A P, Feener C, and Kunkel L M. (1987). Complete cloning of the Duchenne muscular dystrophy (DMD) cDNA and preliminary genomic organization of the DMD gene in normal and affected individuals. Cell 50: 509-517.
5. Yoshida M, and Ozawa E. (1990). Glycoprotein complex anchoring dystrophin to sarcolemma. J Biochem (Tokyo) 108: 748-752.
6. Hoffman E P, Brown R H, Jr., and Kunkel L M. (1987). Dystrophin: the protein product of the Duchenne muscular dystrophy locus. Cell 51: 919-928.
7. Lu Q L, et al. (2003). Functional amounts of dystrophin produced by skipping the mutated exon in the mdx dystrophic mouse. Nat Med 8: 1009-1014.

8. van Deutekom J C, and van Ommen G J. (2003). Advances in Duchenne muscular dystrophy gene therapy. Nat Rev Genet 4: 774-783.
9. Aartsma-Rus A, et al. (2003). Therapeutic antisense-induced exon skipping in cultured muscle cells from six different DMD patients. Hum Mol Genet 12: 907-914.
10. van Deutekom J C, et al. (2001). Antisense-induced exon skipping restores dystrophin expression in DMD patient derived muscle cells. Hum Mol Genet 10: 1547-1554.
11. Aartsma-Rus A, et al. (2004). Antisense-induced multi-exon skipping for duchenne muscular dystrophy makes more sense. Am J Hum Genet 74: 83-92.
12. Bremmer-Bout M, et al. (2004). Targeted Exon Skipping in Transgenic hDMD Mice: a Model for Direct Pre-clinical Screening of Human-specific Antisense Oligonucleotides. Molecular Therapy 10: 232-240.
13. Lu Q L, et al. (2005). Systemic delivery of antisense oligoribonucleotide restores dystrophin expression in body-wide skeletal muscles. Proc. Natl. Acad. Sci. U.S.A 102: 198-203.
14. Aartsma-Rus A, Bremmer-Bout M, Janson A, Den Dunnen J, van Ommen G, and van Deutekom J. (2002). Targeted exon skipping as a potential gene correction therapy for Duchenne muscular dystrophy. Neuromuscul Disord 12: S71-S77.
15. Aartsma-Rus A, et al. (2005). Functional analysis of 114 exon-internal AONs for targeted DMD exon skipping: indication for steric hindrance of SR protein binding sites. Oligonucleotides 15: 284-297.
16. Stojdl D F, and Bell J C. (1999). SR protein kinases: the splice of life. Biochem Cell Biol 77: 293-298.
17. Fokkema I F, den Dunnen J T, and Taschner P E. (2005). LOVD: easy creation of a locus-specific sequence variation database using an "LSDB-in-a-box" approach. Hum. Mutat. 26: 63-68.
18. England S B, et al. (1990). Very mild muscular dystrophy associated with the deletion of 46% of dystrophin. Nature 343: 180-182.
19. Mirabella M, et al. (1998). Giant dystrophin deletion associated with congenital cataract and mild muscular dystrophy. Neurology 51: 592-595.
20. Bushby K M, Appleton R, Anderson L V, Welch J L, Kelly P, and Gardner-Medwin D. (1995). Deletion status and intellectual impairment in Duchenne muscular dystrophy. Dev Med Child Neurol 37: 260-269.
21. Tennyson C N, Klamut H J, and Worton R G. (1995). The human dystrophin gene requires 16 hours to be transcribed and is cotranscriptionally spliced. Nat Genet 9: 184-190.
22. Havenga M J, et al. (2002). Exploiting the natural diversity in adenovirus tropism for therapy and prevention of disease. J Virol 76: 4612-4620.

The invention claimed is:

1. An AON comprising a sequence selected from the group consisting of: SEQ ID NO:115 to SEQ ID NO:118.

2. The AON of claim 1, wherein the AON comprises 14-40 nucleotides.

3. The AON of claim 1, wherein the AON comprises 14-25 nucleotides.

4. The AON of claim 1, wherein the AON comprises one or more modifications selected from the group consisting of: 2'-O-methyl oligoribonucleotides, phosphorothioate backbone, morpholino phosphorodiamidate DNA (morpholinos), locked nucleic acids (LNA); and ethylene bridged nucleic acids (ENA).

5. A method of treating a subject in need thereof, wherein said subject comprises Duchenne Muscular Dystrophy, comprising administering the AON of claim 1 to the subject and wherein said AON induces the exclusion of exon 33 or 44 from a DMD pre-mRNA in said subject.

6. A pharmaceutical composition comprising the AON of claim 1 in combination with a suitable carrier.

7. A method of inducing the exclusion of an exon from a pre-mRNA associated with Duchenne Muscular Dystrophy in a subjecting having Duchenne Muscular Dystrophy, said method comprising administering the AON of claim 1 to the subject.

* * * * *

```
                          SEQUENCE LISTING

<160> NUMBER OF SEQ ID NOS: 128

<210> SEQ ID NO 1
<211> LENGTH: 24
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h2AON1

<400> SEQUENCE: 1
cccauuuugu gaauguuuuc uuuu                                            24

<210> SEQ ID NO 2
<211> LENGTH: 22
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h2AON2

<400> SEQUENCE: 2
uugugcauuu acccauuuug ug                                              22

<210> SEQ ID NO 3
<211> LENGTH: 24
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h2AON3

<400> SEQUENCE: 3
```

-continued gaaaauugug cauuuaccca uuuu                                                    24

<210> SEQ ID NO 4
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h8AON1

<400> SEQUENCE: 4
cuuccuggau ggcuucaau                                                          19

<210> SEQ ID NO 5
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h8AON3

<400> SEQUENCE: 5
guacauuaag auggacuuc                                                          19

<210> SEQ ID NO 6
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h17AON1

<400> SEQUENCE: 6
ccauuacagu ugucuguguu                                                         20

<210> SEQ ID NO 7
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h17AON2

<400> SEQUENCE: 7
uaaucugccu cuucuuuugg                                                         20

<210> SEQ ID NO 8
<211> LENGTH: 16
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h19AON

<400> SEQUENCE: 8
ucugcuggca ucuugc                                                             16

<210> SEQ ID NO 9
<211> LENGTH: 20

```
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h29AON1

<400> SEQUENCE: 9
uauccucuga augucgcauc                                                    20

<210> SEQ ID NO 10
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h29AON2

<400> SEQUENCE: 10
gguuauccuc ugaaugucgc                                                    20

<210> SEQ ID NO 11
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h29AON4

<400> SEQUENCE: 11
ccaucuguua gggucugug                                                     19

<210> SEQ ID NO 12
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h29AON6

<400> SEQUENCE: 12
ucugugccaa uaugcgaauc                                                    20

<210> SEQ ID NO 13
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h29AON9

<400> SEQUENCE: 13
uuaaaugucu caaguucc                                                      18

<210> SEQ ID NO 14
<211> LENGTH: 16
<212> TYPE: RNA
<213> ORGANISM: Artificial
<220> FEATURE:
<223> OTHER INFORMATION: synthetic construct
<220> FEATURE:
```

```
<221> NAME/KEY: misc_feature
<223> OTHER INFORMATION: h29AON10

<400> SEQUENCE: 14
guaguucccu ccaacg                                              16

<210> SEQ ID NO 15
<211> LENGTH: 15
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h29AON11

<400> SEQUENCE: 15
cauguaguuc ccucc                                               15

<210> SEQ ID NO 16
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h40AON1

<400> SEQUENCE: 16
gagccuuuuu ucuucuuug                                           19

<210> SEQ ID NO 17
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h40AON2

<400> SEQUENCE: 17
uccuuucauc ucugggcuc                                           19

<210> SEQ ID NO 18
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h41AON1

<400> SEQUENCE: 18 cucccucuuuc uucuucugc                                          19

<210> SEQ ID NO 19
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h41AON2

<400> SEQUENCE: 19
```

-continued cuucgaaacu gagcaaauuu  20

<210> SEQ ID NO 20
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h42AON1

<400> SEQUENCE: 20
cuugugagac augagug  17

<210> SEQ ID NO 21
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h42AON2

<400> SEQUENCE: 21
cagagacucc ucuugcuu  18

<210> SEQ ID NO 22
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h43AON1

<400> SEQUENCE: 22
ugcugcuguc uucuugcu  18

<210> SEQ ID NO 23
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h43AON2

<400> SEQUENCE: 23
uuguuaacuu uuucccauu  19

<210> SEQ ID NO 24
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h43AON3

<400> SEQUENCE: 24
uguuaacuuu uucccauugg  20

<210> SEQ ID NO 25
<211> LENGTH: 20

```
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h43AON4

<400> SEQUENCE: 25
cauuuuguua acuuuuccc                                                20

<210> SEQ ID NO 26
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h43AON5

<400> SEQUENCE: 26
cuguagcuuc acccuuucc                                                19

<210> SEQ ID NO 27
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h44AON1

<400> SEQUENCE: 27
cgccgccauu ucucaacag                                                19

<210> SEQ ID NO 28
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h44AON2

<400> SEQUENCE: 28
uuuguauuua gcauguuccc                                               20

<210> SEQ ID NO 29
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h45AON1

<400> SEQUENCE: 29
gcugaauuau uucuucccc                                                19

<210> SEQ ID NO 30
<211> LENGTH: 19
<212> TYPE: RNA
<213> ORGANISM: Artificial
<220> FEATURE:
<223> OTHER INFORMATION: synthetic construct
<220> FEATURE:
```

```
<221> NAME/KEY: misc_feature
<223> OTHER INFORMATION: h45AON2

<400> SEQUENCE: 30
uuuuucuguc ugacagcug                                                    19

<210> SEQ ID NO 31
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h45AON3

<400> SEQUENCE: 31
ucuguuuuug aggauugc                                                     18

<210> SEQ ID NO 32
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h45AON4

<400> SEQUENCE: 32
ccaccgcaga uucaggc                                                      17

<210> SEQ ID NO 33
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h45AON5

<400> SEQUENCE: 33
gcccaaugcc auccugg                                                      17

<210> SEQ ID NO 34
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h45AON9

<400> SEQUENCE: 34
uuugcagacc uccugcc                                                      17

<210> SEQ ID NO 35
<211> LENGTH: 15
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h46AON4

<400> SEQUENCE: 35
```

```
cugcuuccuc caacc                                                        15

<210> SEQ ID NO 36
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h46AON6

<400> SEQUENCE: 36
guuaucugcu uccuccaacc                                                   20

<210> SEQ ID NO 37
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h46AON8

<400> SEQUENCE: 37
gcuuuucuuu uaguugcugc                                                   20

<210> SEQ ID NO 38
<211> LENGTH: 15
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h46AON9

<400> SEQUENCE: 38
uuaguugcug cucuu                                                        15

<210> SEQ ID NO 39
<211> LENGTH: 21
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h46AON20

<400> SEQUENCE: 39
gaaauucuga caagauauuc u                                                 21

<210> SEQ ID NO 40
<211> LENGTH: 15
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h46AON21

<400> SEQUENCE: 40
uaaaacaaau ucauu                                                        15

<210> SEQ ID NO 41
<211> LENGTH: 20
```

```
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h46AON22

<400> SEQUENCE: 41
uccagguuca agugggauac                                                    20

<210> SEQ ID NO 42
<211> LENGTH: 15
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h46AON23

<400> SEQUENCE: 42
uuccagguuc aagug                                                         15

<210> SEQ ID NO 43
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h46AON24

<400> SEQUENCE: 43
ucaagcuuuu cuuuuag                                                       17

<210> SEQ ID NO 44
<211> LENGTH: 16
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h46AON25

<400> SEQUENCE: 44
cugacaagau auucuu                                                        16

<210> SEQ ID NO 45
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h46AON26

<400> SEQUENCE: 45
agguucaagu gggauacua                                                     19

<210> SEQ ID NO 46
<211> LENGTH: 18
<212> TYPE: RNA
<213> ORGANISM: Artificial
<220> FEATURE:
<223> OTHER INFORMATION: synthetic construct
<220> FEATURE:
```

```
<221> NAME/KEY: misc_feature
<223> OTHER INFORMATION: h47AON1

<400> SEQUENCE: 46
ucuugcucuu cugggcuu                                                    18

<210> SEQ ID NO 47
<211> LENGTH: 21
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h47AON2

<400> SEQUENCE: 47
cuugagcuua uuuucaaguu u                                                21

<210> SEQ ID NO 48
<211> LENGTH: 22
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h47AON3

<400> SEQUENCE: 48
uccaguuuca uuuaauuguu ug                                               22

<210> SEQ ID NO 49
<211> LENGTH: 23
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h47AON4

<400> SEQUENCE: 49
cugcuugagc uuauuuucaa guu                                              23

<210> SEQ ID NO 50
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h47AON5

<400> SEQUENCE: 50
agcacuuaca agcacgggu                                                   19

<210> SEQ ID NO 51
<211> LENGTH: 21
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h47AON6

<400> SEQUENCE: 51
```
uucaaguuua ucuugcucuu c					21

<210> SEQ ID NO 52
<211> LENGTH: 16
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h48AON1

<400> SEQUENCE: 52
uuucuccuug uuucuc					16

<210> SEQ ID NO 53
<211> LENGTH: 21
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h48AON2

<400> SEQUENCE: 53
uuauaaauuu ccaacugauu c					21

<210> SEQ ID NO 54
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h48AON3

<400> SEQUENCE: 54
ggucuuuuau uugagcuuc					19

<210> SEQ ID NO 55
<211> LENGTH: 21
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h48AON4

<400> SEQUENCE: 55
cuucaagcuu uuuuucaagc u					21

<210> SEQ ID NO 56
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h48AON6

<400> SEQUENCE: 56
gcuucaauuu cuccuuguu					19

<210> SEQ ID NO 57
<211> LENGTH: 19

```
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h48AON7

<400> SEQUENCE: 57
uuuauuugag cuucaauuu                                              19

<210> SEQ ID NO 58
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h48AON8

<400> SEQUENCE: 58
gcugcccaag gucuuuu                                                17

<210> SEQ ID NO 59
<211> LENGTH: 21
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h48AON9

<400> SEQUENCE: 59
cuucaagguc uucaagcuuu u                                           21

<210> SEQ ID NO 60
<211> LENGTH: 21
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h48AON10

<400> SEQUENCE: 60
uaacugcucu ucaaggucuu c                                           21

<210> SEQ ID NO 61
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h49AON1

<400> SEQUENCE: 61
cuuccacauc cgguuguuu                                              19

<210> SEQ ID NO 62
<211> LENGTH: 19
<212> TYPE: RNA
<213> ORGANISM: Artificial
<220> FEATURE:
<223> OTHER INFORMATION: synthetic construct
<220> FEATURE:
```

```
<221> NAME/KEY: misc_feature
<223> OTHER INFORMATION: h49AON2

<400> SEQUENCE: 62
guggcugguu uuccuugu                                                 19

<210> SEQ ID NO 63
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h50AON1

<400> SEQUENCE: 63
cucagagcuc agaucuu                                                  17

<210> SEQ ID NO 64
<211> LENGTH: 15
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h50AON2

<400> SEQUENCE: 64
ggcugcuuug cccuc                                                    15

<210> SEQ ID NO 65
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h51AON1

<400> SEQUENCE: 65
ucaaggaaga uggcauuucu                                               20

<210> SEQ ID NO 66
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h51AON24

<400> SEQUENCE: 66
gaaagccagu cgguaaguuc                                               20

<210> SEQ ID NO 67
<211> LENGTH: 15
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h51AON27

<400> SEQUENCE: 67
```

```
cacccaccau caccc                                              15

<210> SEQ ID NO 68
<211> LENGTH: 23
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h51AON2

<400> SEQUENCE: 68
ccucugugau uuuauaacuu gau                                     23

<210> SEQ ID NO 69
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h51AON29

<400> SEQUENCE: 69
ugauauccuc aaggucaccc                                         20

<210> SEQ ID NO 70
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h52AON1

<400> SEQUENCE: 70
uugcuggucu uguuuuc                                            18

<210> SEQ ID NO 71
<211> LENGTH: 16
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h52AON2

<400> SEQUENCE: 71
ccguaaugau uguucu                                             16

<210> SEQ ID NO 72
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h53AON1

<400> SEQUENCE: 72
cuguugccuc cgguucug                                           18

<210> SEQ ID NO 73
<211> LENGTH: 18
```

```
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h53AON2

<400> SEQUENCE: 73
uuggcucugg ccuguccu                                                   18

<210> SEQ ID NO 74
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h54AON1

<400> SEQUENCE: 74
uacauuuguc ugccacugg                                                  19

<210> SEQ ID NO 75
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h54AON2

<400> SEQUENCE: 75
cccggagaag uuucaggg                                                   18

<210> SEQ ID NO 76
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h55AON1

<400> SEQUENCE: 76
cuguugcagu aaucuaugag                                                 20

<210> SEQ ID NO 77
<211> LENGTH: 23
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h55AON2

<400> SEQUENCE: 77
ugccauuguu ucaucagcuc uuu                                             23

<210> SEQ ID NO 78
<211> LENGTH: 20
<212> TYPE: RNA
<213> ORGANISM: Artificial
<220> FEATURE:
<223> OTHER INFORMATION: synthetic construct
<220> FEATURE:
```

```
<221> NAME/KEY: misc_feature
<223> OTHER INFORMATION: h55AON3

<400> SEQUENCE: 78
ugcaguaauc uaugaguuuc                                           20

<210> SEQ ID NO 79
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h55AON5

<400> SEQUENCE: 79
uccuguagga cauuggcagu                                           20

<210> SEQ ID NO 80
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h55AON6

<400> SEQUENCE: 80
gagucuucua ggagccuu                                             18

<210> SEQ ID NO 81
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h56AON1

<400> SEQUENCE: 81
uuuuuuggcu guuuucaucc                                           20

<210> SEQ ID NO 82
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h56AON2

<400> SEQUENCE: 82
guucacucca cuugaaguuc                                           20

<210> SEQ ID NO 83
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h56AON3

<400> SEQUENCE: 83
```

```
ccuuccaggg aucucagg                                                    18

<210> SEQ ID NO 84
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h57AON1

<400> SEQUENCE: 84
uaggugccug ccggcuu                                                     17

<210> SEQ ID NO 85
<211> LENGTH: 21
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h57AON2

<400> SEQUENCE: 85
cugaacugcu ggaaagucgc c                                                21

<210> SEQ ID NO 86
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h57AON3

<400> SEQUENCE: 86
uucagcugua gccacacc                                                    18

<210> SEQ ID NO 87
<211> LENGTH: 22
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h58AON1

<400> SEQUENCE: 87
uucuuuaguu uucaauuccc uc                                               22

<210> SEQ ID NO 88
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h58AON2

<400> SEQUENCE: 88
gaguuucucu aguccuucc                                                   19

<210> SEQ ID NO 89
<211> LENGTH: 21
```

-continued

```
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h59AON1

<400> SEQUENCE: 89
caauuuuucc cacucaguau u                                           21

<210> SEQ ID NO 90
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h59AON2

<400> SEQUENCE: 90
uugaaguucc uggagucuu                                              19

<210> SEQ ID NO 91
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h60AON1

<400> SEQUENCE: 91
guucucuuuc agaggcgc                                               18

<210> SEQ ID NO 92
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h60AON2

<400> SEQUENCE: 92
gugcugaggu uauacggug                                              19

<210> SEQ ID NO 93
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h61AON1

<400> SEQUENCE: 93
gucccugugg gcuucaug                                               18

<210> SEQ ID NO 94
<211> LENGTH: 18
<212> TYPE: RNA
<213> ORGANISM: Artificial
<220> FEATURE:
<223> OTHER INFORMATION: synthetic construct
<220> FEATURE:
```

```
<221> NAME/KEY: misc_feature
<223> OTHER INFORMATION: h61AON2

<400> SEQUENCE: 94
gugcugagau gcuggacc                                                    18

<210> SEQ ID NO 95
<211> LENGTH: 16
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h62AON1

<400> SEQUENCE: 95
uggcucucuc ccaggg                                                      16

<210> SEQ ID NO 96
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h62AON2

<400> SEQUENCE: 96
gggcacuuug uuuggcg                                                     17

<210> SEQ ID NO 97
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h63AON1

<400> SEQUENCE: 97
ggucccagca aguuguuug                                                   19

<210> SEQ ID NO 98
<211> LENGTH: 21
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h63AON2

<400> SEQUENCE: 98
guagagcucu gucauuuugg g                                                21

<210> SEQ ID NO 99
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h71AON1

<400> SEQUENCE: 99
```

-continued

| | |
|---|---|
| gccagaaguu gaucagagu | 19 |

<210> SEQ ID NO 100
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h71AON2

<400> SEQUENCE: 100

| | |
|---|---|
| ucuacuggcc agaaguug | 18 |

<210> SEQ ID NO 101
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h72AON1

<400> SEQUENCE: 101

| | |
|---|---|
| ugaguaucau cgugugaaag | 20 |

<210> SEQ ID NO 102
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h72AON2

<400> SEQUENCE: 102

| | |
|---|---|
| gcauaauguu caaugcgug | 19 |

<210> SEQ ID NO 103
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h73AON1

<400> SEQUENCE: 103

| | |
|---|---|
| gauccauugc uguuuucc | 18 |

<210> SEQ ID NO 104
<211> LENGTH: 21
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h73AON2

<400> SEQUENCE: 104

| | |
|---|---|
| gagaugcuau cauuuagaua a | 21 |

<210> SEQ ID NO 105
<211> LENGTH: 17

```
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h74AON1

<400> SEQUENCE: 105
cuggcucagg ggggagu                                                   17

<210> SEQ ID NO 106
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h74AON2

<400> SEQUENCE: 106
uccccucuuu ccucacucu                                                 19

<210> SEQ ID NO 107
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h75AON1

<400> SEQUENCE: 107
ccuuuauguu cgugcugcu                                                 19

<210> SEQ ID NO 108
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h75AON2

<400> SEQUENCE: 108
ggcggccuuu guguugac                                                  18

<210> SEQ ID NO 109
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h76AON1

<400> SEQUENCE: 109
gagagguaga aggagagga                                                 19

<210> SEQ ID NO 110
<211> LENGTH: 19
<212> TYPE: RNA
<213> ORGANISM: Artificial
<220> FEATURE:
<223> OTHER INFORMATION: synthetic construct
<220> FEATURE:
```

```
<221> NAME/KEY: misc_feature
<223> OTHER INFORMATION: h76AON2

<400> SEQUENCE: 110
auaggcugac ugcugucgg                                              19

<210> SEQ ID NO 111
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h77AON1

<400> SEQUENCE: 111
uuguguccug gggagga                                                17

<210> SEQ ID NO 112
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h77AON2

<400> SEQUENCE: 112
ugcuccauca ccuccucu                                               18

<210> SEQ ID NO 113
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h78AON1

<400> SEQUENCE: 113 gcuuccagg gguauuuc                                                18

<210> SEQ ID NO 114
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h78AON2

<400> SEQUENCE: 114
cauuggcuuu ccagggg                                                17

<210> SEQ ID NO 115
<211> LENGTH: 19
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h33AON1

<400> SEQUENCE: 115
```

```
cugacgucca gucuuuauc                                                              19

<210> SEQ ID NO 116
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h33AON2

<400> SEQUENCE: 116
gggauuuucc gucugcuu                                                               18

<210> SEQ ID NO 117
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h44AON3

<400> SEQUENCE: 117
ccgccauuuc ucaacag                                                                17

<210> SEQ ID NO 118
<211> LENGTH: 21
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h44AON4

<400> SEQUENCE: 118
uucucaggaa uuugugucuu u                                                           21

<210> SEQ ID NO 119
<211> LENGTH: 17
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h45AON10

<400> SEQUENCE: 119
caguuugccg cugccca                                                                17

<210> SEQ ID NO 120
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h45AON11

<400> SEQUENCE: 120
guugcauuca auguucugac                                                             20

<210> SEQ ID NO 121
<211> LENGTH: 21
```

```
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h45AON12

<400> SEQUENCE: 121
auuuuuccug uagaauacug g                                              21

<210> SEQ ID NO 122
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h52AON3

<400> SEQUENCE: 122
gcuggucuug uuuuucaa                                                  18

<210> SEQ ID NO 123
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h52AON4

<400> SEQUENCE: 123
uggucuuguu uuucaaauuu                                                20

<210> SEQ ID NO 124
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h52AON5

<400> SEQUENCE: 124
gucuuguuuu ucaaauuuug                                                20

<210> SEQ ID NO 125
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h52AON6

<400> SEQUENCE: 125
cuuguuuuuc aaauuuuggg                                                20

<210> SEQ ID NO 126
<211> LENGTH: 19
<212> TYPE: RNA
<213> ORGANISM: Artificial
<220> FEATURE:
<223> OTHER INFORMATION: synthetic construct
<220> FEATURE:
```

```
<221> NAME/KEY: misc_feature
<223> OTHER INFORMATION: h52AON7

<400> SEQUENCE: 126
uguuuuucaa auuuugggc                                                19

<210> SEQ ID NO 127
<211> LENGTH: 20
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h64AON1

<400> SEQUENCE: 127
uccuauaagc ugagaaucug                                               20

<210> SEQ ID NO 128
<211> LENGTH: 18
<212> TYPE: RNA
<213> ORGANISM: Artificial
<220> FEATURE:
<223> OTHER INFORMATION: synthetic construct
<220> FEATURE:
<221> NAME/KEY: misc_feature
<223> OTHER INFORMATION: h64AON2

<400> SEQUENCE: 128
gccuucugca gucuucgg                                                 18
```